(12) United States Patent
Farnet et al.

(10) Patent No.: US 7,186,713 B2
(45) Date of Patent: Mar. 6, 2007

(54) FARNESYL DIBENZODIAZEPINONES AND METHODS OF TREATING CANCER USING SAME

(75) Inventors: Chris M. Farnet, Outremont (CA); Violetta Dimitriadou, Saint-Anne-de-Bellevue (CA); Brian O. Bachmann, Nashville, TN (US)

(73) Assignee: Ecopia BioSciences, Inc., Saint-Laurent (CA)

( * ) Notice: Subject to any disclaimer, the term of this patent is extended or adjusted under 35 U.S.C. 154(b) by 144 days.

(21) Appl. No.: 10/951,436

(22) Filed: Sep. 27, 2004

(65) Prior Publication Data

US 2005/0107363 A1  May 19, 2005

Related U.S. Application Data

(63) Continuation-in-part of application No. 10/762,107, filed on Jan. 21, 2004, now Pat. No. 7,101,872.

(60) Provisional application No. 60/441,126, filed on Jan. 21, 2003, provisional application No. 60/492,997, filed on Aug. 7, 2003, provisional application No. 60/518,286, filed on Nov. 10, 2003.

(51) Int. Cl.
*A61P 35/00* (2006.01)
(52) U.S. Cl. .................................................. 514/220
(58) Field of Classification Search ................ 514/220
See application file for complete search history.

(56) References Cited

U.S. PATENT DOCUMENTS 5,541,181 A    7/1996  Ohkuma et al. ............ 514/220

2003/0109518 A1   6/2003  Lu et al. ..................... 514/221
2003/0219718 A1  11/2003  Weber et al. .................. 435/4
2004/0220179 A1  11/2004  Lu et al. ................ 514/217.03

FOREIGN PATENT DOCUMENTS

CA        2248820         9/1997

OTHER PUBLICATIONS

Embley and Stackebrandt, Annu. Rev. Microbiol. (1994) 48, pp. 257-289 "The molecular phylogeny and systematics of the actinomycetes".
British Journal of Cancer (1998) vol. 77(1) pp. 1-11 United Kingdom Co-ordinating Committee on Cancer Research (UKCCCR) Guidelines for the Welfare of Animals in Experimental Neoplasia (Second Edition).
Charan et al., Diazepinomicin, a new antimicrobial alkaloid from a marine Micromonospora sp. J. Nat Prod. Aug. 2004;67(8):1431-3.
Charan, et al., "A New Antimicrobial Alkaloid from a Micromonospora sp.", Abstract and Figures from Poster Presentation #p:157 at the 44th Annual Meeting of the American Society of Pharmacognosy, Chapel Hill, N.C., Jul. 12-16, 2003.
Yasuhiro Igarashi, et al., Revision of the Structure Assigned to the Antibiotic BU-4664L from Micromonopora, *J. Antibiot.* 58(5): 350-352 (2005).
Correction to Article by Yashuhiro Igarashi et al., Revision of the Structure Assigned to the Antibiotic BU-4664L from Micromonopora, *J. Antibiot.* 58(7) (2005).

*Primary Examiner*—Bruck Kifle
(74) *Attorney, Agent, or Firm*—Kathleen M. Williams; Mark J. FitzGerald; Edwards Angell Palmer & Dodge, LLP

(57) ABSTRACT

This invention relates to methods of inhibiting growth of a cancer cell and methods of treating cancer using a novel farnesylated dibenzodiazepinone.

34 Claims, 17 Drawing Sheets

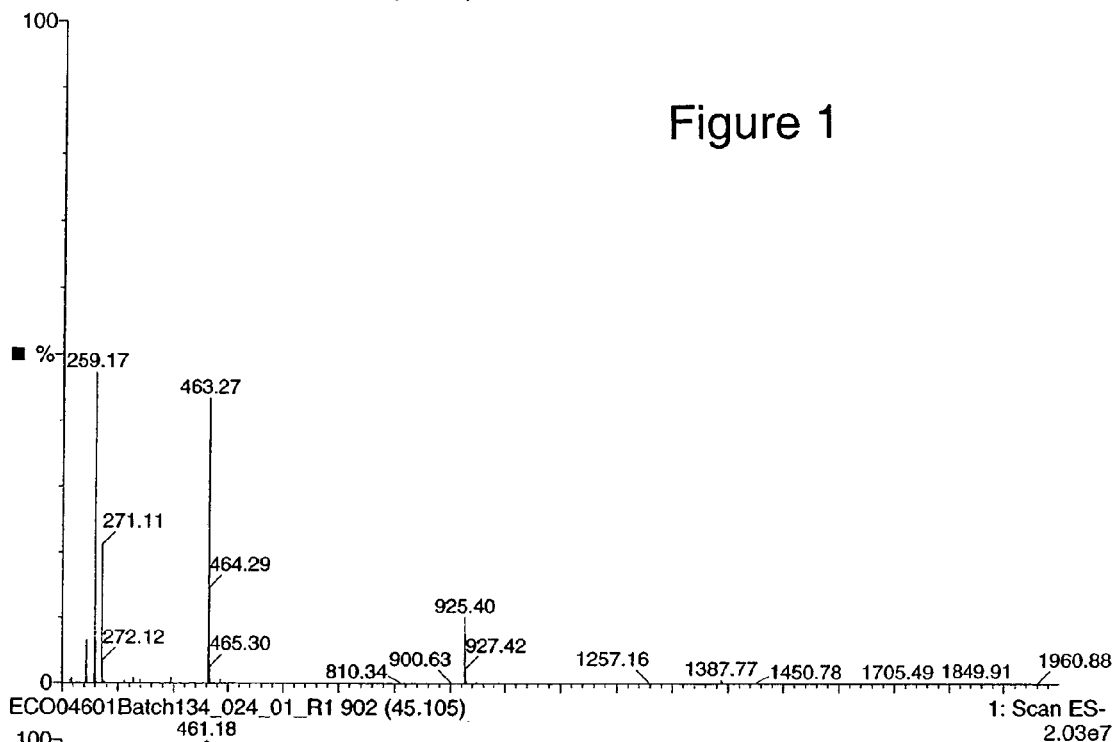
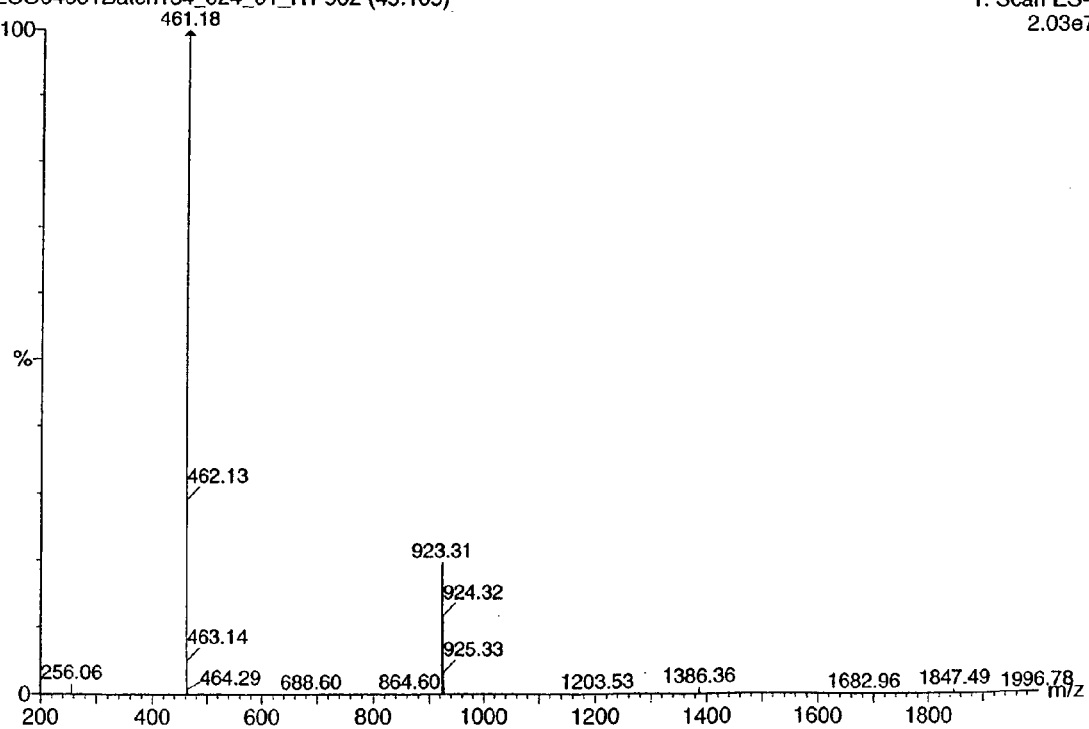
Figure 1

Figure 12

| RT | Response | Ar/Ht | RFact | ECL | Peak Name | Percent | Comment 1 | Comment 2 |
|---|---|---|---|---|---|---|---|---|
| 1.630 | 4.486E+8 | 0.026 | --- | 7.012 | Solvent Peak | --- | < min rt | |
| 1.874 | 754 | 0.024 | --- | 7.505 | | --- | < min rt | |
| 2.521 | 1314 | 0.026 | --- | 8.810 | | --- | < min rt | |
| 8.150 | 16710 | 0.041 | 0.980 | 14.621 | 15:0 ISO | 26.83 | ECL deviates 0.000 | Reference 0.000 |
| 8.288 | 3943 | 0.042 | 0.977 | 14.711 | 15:0 ANTEISO | 6.32 | ECL deviates 0.000 | Reference 0.001 |
| 9.767 | 2378 | 0.042 | 0.956 | 15.627 | 16: ISO | 3.73 | ECL deviates 0.001 | Reference -0.001 |
| 10.086 | 1692 | 0.047 | 0.953 | 15.819 | 16:1 CIS 9 | 2.64 | ECL deviates 0.002 | Reference |
| 10.385 | 2413 | 0.045 | 0.949 | 15.999 | 16:0 | 3.75 | ECL deviates -0.001 | Reference -0.003 |
| 11.106 | 11222 | 0.044 | 0.941 | 16.417 | 16:0 9? METHYL | 17.31 | ECL deviates 0.001 | Reference |
| 11.475 | 8905 | 0.046 | 0.937 | 16.630 | 17:0 ISO | 13.68 | ECL deviates 0.001 | Reference 0.000 |
| 11.634 | 11190 | 0.046 | 0.936 | 16.722 | 17:0 ANTEISO | 17.17 | ECL deviates 0.000 | Reference -0.001 |
| 11.757 | 2741 | 0.046 | 0.935 | 16.793 | 17:1 CIS 9 | 4.20 | ECL deviates 0.001 | Reference |
| 13.468 | 2898 | 0.049 | 0.920 | 17.771 | 18:1 CIS 9 | 4.37 | ECL deviates 0.002 | Reference |

ECL Deviation: 0.001
Total Response: 64093
Percent Named: 100.00%

Reference ECL Shift: 0.001
Total Named: 64093
Total Amount: 61014

Number Reference peaks: 6

Matches:

| Library | Sim Index | Entry Name |
|---|---|---|
| ACTIN3 1.07 | 0.293 | *Micromonospora chalcea* |

Alignment:

| | | |
|---|---|---|
| 0.00 | % | 499 | Micromonospora chalcea |
| 1.00 | % | 499 | Micromonospora aurantiaca |
| 1.50 | % | 499 | Micromonospora nigra |
| 1.60 | % | 499 | Micromonospora halophytica nigra |
| 1.60 | % | 499 | Micromonospora fusca |
| 1.60 | % | 499 | Micromonospora brunnea |
| 1.80 | % | 499 | Micromonospora halophytica halophytica |
| 1.80 | % | 499 | Micromonospora sagamiensis flava |
| 2.00 | % | 499 | Micromonospora pallida |
| 2.00 | % | 499 | Micromonospora sagamiensis nonreductans |

Figure 14
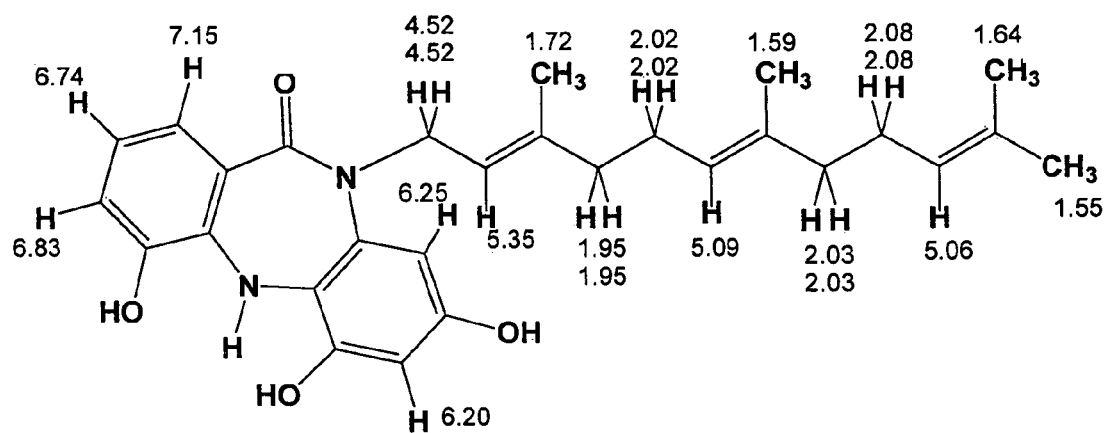
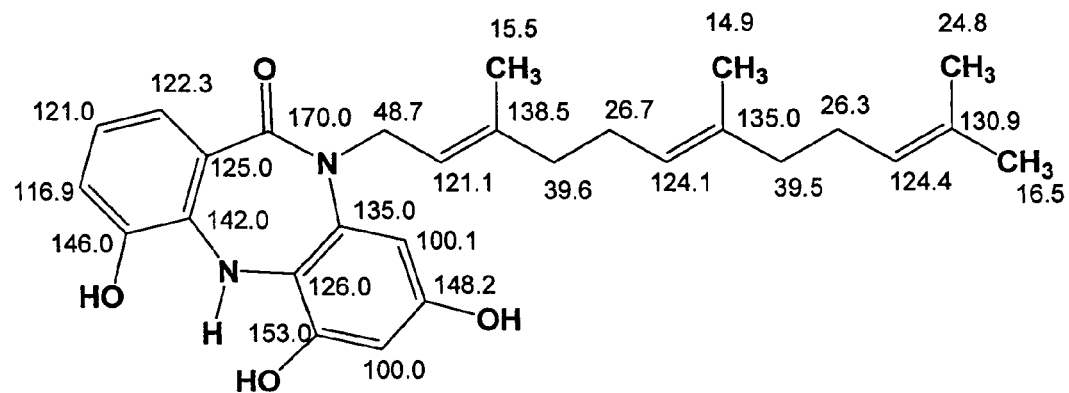

Antitumor efficacy of ECO-4601 against orthotopic C6 glioma tumor xenograft

FARNESYL DIBENZODIAZEPINONES AND METHODS OF TREATING CANCER USING SAME

RELATED APPLICATIONS

This application is a CIP of U.S. application Ser. No. 10/762,107, filed Jan. 21, 2004, now U.S. Pat. No. 7,101,872 which claims priority to U.S. Provisional Application 60/441,126, filed Jan. 21, 2003; U.S. Provisional Application 60/492,997, filed Aug. 7, 2003; and U.S. Provisional Application 60/518,286, filed Nov. 10, 2003. The entire teachings of the above applications are incorporated herein by reference.

FIELD OF THE INVENTION

This invention relates methods of inhibiting proliferation of a cancer cell and methods of treating cancer in a mammal using the compound of Formula II or its pharmaceutically acceptable salts.

BACKGROUND OF THE INVENTION

Cancer is a disease in which normal body cells are changed, becoming able to multiply without regard to normal cellular restraints and to invade and colonize areas of the body normally occupied by other cells. See B. Alberts et al., Molecular Biology of the Cell 1255–1294 (3d ed. 1994). According to the American Cancer Society, one-half of all American men and one-third of all American women will at some point in their lives develop cancer.

Due to the ability of cancer cells to spread and rapidly proliferate, it is difficult to treat cancer patients by attempting to selectively kill cancerous cells. Some have compared the difficulty of this task to the difficulty of completely ridding a garden of weeds. As with weeds, if only a few cancer cells are left untouched by treatment, they may again spread throughout the body, causing a recurrence of the disease. Current treatments for cancer include surgery and therapies using chemicals and radiation. The effectiveness of these treatments is often limited, however, since cancer cells that have spread from the original tumor site may be missed by surgery and radiation, and since chemical treatments which kill or disable cancer cells are often capable of causing similar damage to normal cells.

From the foregoing, it will be appreciated that there is a need in the art for novel cancer therapeutics which have higher efficacy, specificity, or reduced side effects.

SUMMARY OF THE INVENTION

The invention encompasses a method of inhibiting the growth of a cancer cell, the method comprising contacting the cancer cell with a therapeutically effective amount of compound of formula II:

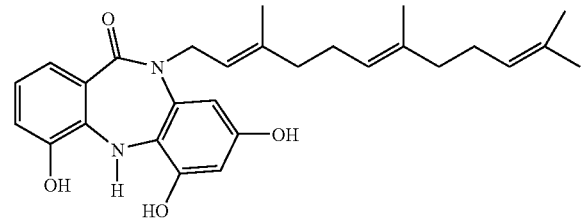

such that growth of the cancer cell is inhibited.

In another aspect, the invention provides method of inhibiting the growth of a cancer cell, the method comprising contacting the cancer cell with a therapeutically effective amount of compound of formula I:

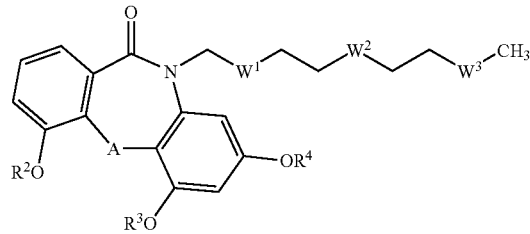

such that growth of the cancer cell is inhibited.

$W^1$, $W^2$ and $W^3$ is each independently selected from

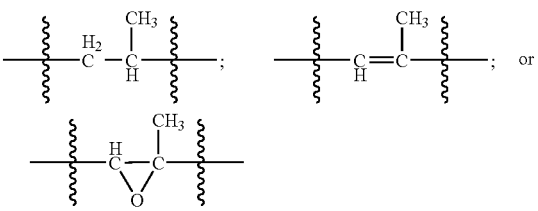

A is selected from —NH—, —NCH$_2$R$^1$, —NC(O)R$^1$;

R$^1$ is selected from C$_{1-6}$ alkyl, C$_{2-6}$ alkene, aryl or heteroaryl;

R$^2$, R$^3$, and R$^4$ is each independently selected from H, R$^5$, —C(O)R$^6$ R$^5$ is each independently selected from C$_{1-6}$ alkyl, C$_{2-7}$ alkalene, aryl or heteroaryl;

R$^6$ is each independently selected from H, C$_{1-6}$ alkyl, C$_{2-7}$ alkalene, aryl or heteroaryl; or a pharmaceutically acceptable salt thereof, such that growth of the cancer cell is inhibited.

In one embodiment of this aspect, A of the compound is NH, —NCH$_2$R$^1$, or —NC(O)R$^1$. In another embodiment, R$^2$ of the compound is H. In yet another embodiment, R$^3$ of the compound is H. In still another embodiment, R$^4$ of the compound is H. The present invention further contemplates an embodiment of this aspect in which R$^2$, R$^3$ and R$^4$ of the compound are each H. In another embodiment, R$^2$, R$^3$ and R$^4$ can each be H, and W$^1$ can be —CH=CH—. In yet another embodiment, R$^2$, R$^3$ and R$^4$ of the compound are each H, and W$^2$ is —CH=CH—. The R$^2$, R$^3$ and R$^4$ of the compound can each be H, and W$^3$—CH=CH—. Alternatively, A of the compound can be NH and R$^2$, R$^3$ and R$^4$ are each H. In yet another embodiment, A is NH, and each of W$^1$, W$^2$, and W$^3$ is —CH=CH—.

The invention further encompasses a method of treating a pre-cancerous or cancerous condition in a mammal, comprising the step of administering to the mammal a therapeutically effective amount of the compound of formula II:

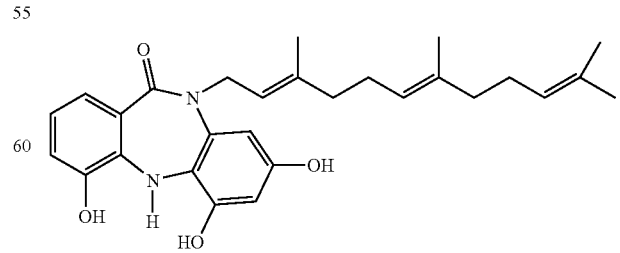

such that a pre-cancerous or cancerous condition is treated.

In another aspect, the invention provides a method of treating a pre-cancerous or cancerous condition in a mammal, comprising the step of administering to the mammal a therapeutically effective amount of the compound of formula I:

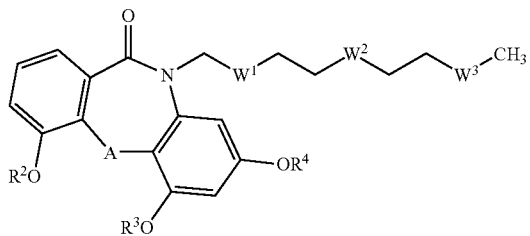

such that a pre-cancerous or cancerous condition is treated.

$W^1$, $W^2$ and $W^3$ is each independently selected from

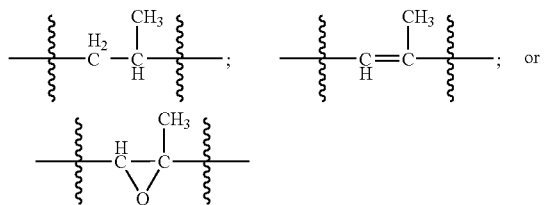

A is selected from —NH—, —NCH$_2$R$^1$, —NC(O)R$^1$;

R$^1$ is selected from C$_{1-6}$ alkyl, C$_{2-6}$ alkene, aryl or heteroaryl;

R$^2$, R$^3$, and R$^4$ is each independently selected from H, R$^5$, —C(O)R$^6$ R$^5$ is each independently selected from C$_{1-6}$ alkyl, C$_{2-7}$ alkalene, aryl or heteroaryl;

R$^6$ is each independently selected from H, C$_{1-6}$ alkyl, C$_{2-7}$ alkalene, aryl or heteroaryl; or a pharmaceutically acceptable salt thereof, to a mammal comprising a cancer cell, such that a pre-cancerous or cancerous condition is treated.

In one embodiment of this aspect, A of the compound is NH, —NCH$_2$R$^1$, or —NC(O)R$^1$. In another embodiment, R$^2$ of the compound is H. In yet another embodiment, R$^3$ of the compound is H. In still another embodiment, R$^4$ of the compound is H. The present invention further contemplates an embodiment of this aspect in which R$^2$, R$^3$ and R$^4$ of the compound are each H. In another embodiment, R$^2$, R$^3$ and R$^4$ can each be H, and W$^1$ can be —CH=CH—. In yet another embodiment, R$^2$, R$^3$ and R$^4$ of the compound are each H, and W$^2$ is —CH=CH—. The R$^2$, R$^3$ and R$^4$ of the compound can each be H, and W$^3$—CH=CH—. Alternatively, A of the compound can be NH and R$^2$, R$^3$ and R$^4$ are each H. In yet another embodiment, A is NH, and each of W$^1$, W$^2$, and W$^3$ is —CH=CH—.

In one embodiment, the cancer is selected from the group consisting of lung cancer, colon cancer, brain cancer, ovarian cancer, renal cancer, prostate cancer, breast cancer, and melanoma.

According to one embodiment of this aspect, the compound is administered orally. In another embodiment, the compound is administered intravenously. In still another embodiment, the compound is administered intraperitoneally.

BRIEF DESCRIPTION OF THE FIGURES

FIG. 1 shows the mass of the compound of Formula II determined by electrospray mass spectrometry to be 462.6.

FIG. 12 shows results of the fatty acid analysis of Micromonospora sp. strain 046ECO11 (Accession No. IDAC 070303-01). Analysis was conducted using gas chromatography on fatty acid methyl esters (FAME).

FIG. 14 shows the complete $^1$H and $^{13}$C NMR assignments for the compound of formula II when measured in MeOH-d4.

DETAILED DESCRIPTION OF THE INVENTION

Figure 13:
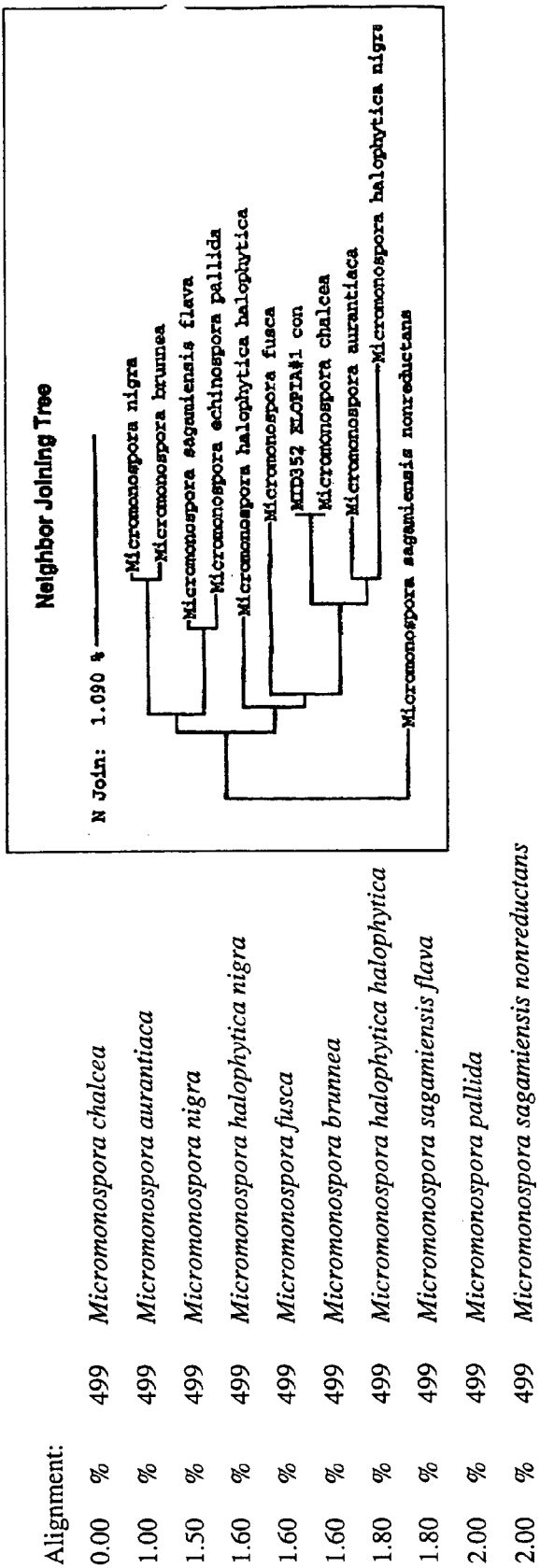
FIG. 13 illustrates the 16S ribosomal RNA analysis of Micromonospora sp. strain 046ECO11 (Accession No. IDAC 070303-01). Alignment of 16S ribosomal RNA sequences demonstrates the phylogenetic relatedness of Micromonospora sp. strain 046ECO11 (indicated as MID352 ECOPIA#1 con) to Micromonospora chalcea.

The present invention relates to a method of inhibiting proliferation and/or growth of a cancer cell. The method comprises contacting the cell with a farnesyl dibenzodiazepinone compounds, such as the compound of formula II, or "ECO-04601," which was isolated from novel strains of actinomycetes, *Micromonospora* sp. strain 046-ECO 11 and strain [S01]046. These microorganisms were analysed using gas chromatography as Fatty acid methyl esters (FAME) (FIG. 12) 6S ribosomal RNA determination (FIG. 13) and were found to belong to the genus of *Micromonospora*. These organisms were deposited on Mar. 7, 2003, and Dec. 23, 2003, respectively, with the International Depository Authority of Canada (IDAC), Bureau of Microbiology, Health Canada, 1015 Arlington Street, Winnipeg, Manitoba, Canada R3E 3R2, under Accession Nos. IDAC 070303-01 and IDAC 231203-01, respectively.

The present invention further relates to methods of treating a pre-cancerous or cancerous condition in a mammal, the method comprising administering a therapeutically effective amount of a farnesyl dibenzodiazepinone compounds, such that the pre-cancerous or cancerous condition is treated. The compound of formula II is useful as a pharmaceutical, in particular for use as an inhibitor of cancer cell growth. Alternatively, a compound of formula I can be used.

The invention further relates to pharmaceutically acceptable salts and derivatives of the compound of formula II, and to methods for obtaining such compounds. One method of obtaining the compound is by cultivating *Micromonospora* sp. strain 046-ECO11, or a mutant or a variant thereof, under suitable *Micromonospora* culture conditions, preferably using the fermentation protocol described hereinbelow.

The present invention also relates to pharmaceutical compositions comprising the compound of formula II and its pharmaceutically acceptable salts and derivatives.

I. Definitions

For convenience, the meaning of certain terms and phrases used in the specification, examples, and appended claims, are provided below.

As used herein, the term "farnesyl dibenzodiazepinone" refers to a class of dibenzodiazepinone compounds containing a farnesyl moiety. The term includes, but is not limited to, the exemplified compound of the present invention, 10-farnesyl-4,6,8-trihydroxy-dibenzodiazepin-11-one, which is referred to herein as the compound of formula II, or "ECO-04601." As used herein, the term "farnesyl dibenzodiazepinone" includes compounds of this class that can be used as intermediates in chemical syntheses. As used herein, the term "alkyl" refers to linear or branched hydrocarbon groups. Examples of alkyl groups include, without limitation, methyl, ethyl, n-propyl, isopropyl, n-butyl, pentyl, hexyl, heptyl, cyclopentyl, cyclohexyl, cyclohexymethyl, and the like. Alkyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, oxo, guanidino and formyl.

The term "alkenyl" refers to linear, branched or cyclic hydrocarbon groups containing at least one carbon-carbon double bond. Examples of alkenyl groups include, without limitation, vinyl, 1-propen-2-yl, 1-buten-4-yl, 2-buten-4-yl, 1-penten-5-yl and the like. Alkenyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration.

The terms "cycloalkyl" and "cycloalkyl ring" refer to a saturated or partially unsaturated carbocyclic ring in a single or fused carbocyclic ring system having from three to fifteen ring members. Examples of cycloalkyl groups include, without limitation, cyclopropyl, cyclobutyl, cyclohexyl, and cycloheptyl. Cycloalkyl may optionally be substituted with substituents selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The terms "heterocyclyl" and "heterocyclic" refer to a saturated or partially unsaturated ring containing one to four hetero atoms or hetero groups selected from O, N, NH, NRx, PO2, S, SO or SO2 in a single or fused heterocyclic ring system having from three to fifteen ring members. Examples of a heterocyclyl or heterocyclic ring include, without limitation, morpholinyl, piperidinyl, and pyrrolidinyl. Heterocyclyl, heterocyclic or heterocyclyl ring may optionally be substituted with substituents selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The term "amino acid" refers to any natural amino acid, all natural amino acids are well known to a person skilled in the art.

The term "halo" refers to a halogen atom, e.g., bromine, chlorine, fluorine and iodine.

The terms "aryl" and "aryl ring" refer to aromatic groups in a single or fused ring system, having from five to fifteen ring members. Examples of aryl include, without limitation, phenyl, naphthyl, biphenyl, terphenyl. Aryl may optionally be substituted with one or more substituent group selected from acyl, amino, acylamino, acyloxy, azido, alkythio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl.

The terms "heteroaryl" and "heteroaryl ring" refer to aromatic groups in a single or fused ring system, having from five to fifteen ring members and containing at least one hetero atom such as O, N, S, SO and SO2. Examples of heteroaryl groups include, without limitation, pyridinyl, thiazolyl, thiadiazoyl, isoquinolinyl, pyrazolyl, oxazolyl, oxadiazoyl, triazolyl, and pyrrolyl groups. Heteroaryl groups may opitionally be substituted with one or more substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl.

The terms "aralkyl" and "heteroaralkyl" refer to an aryl group or a heteroaryl group, respectively bonded directly through an alkyl group, such as benzyl. Aralkyl and heteroaralkyl may be optionally substituted as the aryl and heteroaryl groups.

Similarly, the terms "aralkenyl" and "heteroaralkenyl" refer to an aryl group or a heteroaryl group, respectively bonded directly through an alkene group, such as benzyl.

Aralkenyl and heteroaralkenyl may be optionally substituted as the aryl and heteroaryl groups.

The compounds of the present invention can possess one or more asymmetric carbon atoms and can exist as optical isomers forming mixtures of racemic or non-racemic compounds. The compounds of the present invention are useful as single isomers or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes.

The invention encompasses isolated or purified compounds. An "isolated" or "purified" compound refers to a compound which represents at least 10%, 20%, 50%, 80%. or 90% of the compound of the present invention present in a mixture, provided that the mixture comprising the compound of the invention has demonstrable (i.e. statistically significant). biological activity including antibacterial, cytostatic, cytotoxic, antiinflammatory or enzyme inhibitory action when tested in conventional biological assays known to a person skilled in the art.

The terms "farnesyl dibenzodiazepinone-producing microorganism" and "producer of farnesyl dibenzodiazepinone," as used herein, refer to a microorganism that carries genetic information necessary to produce a farnesyl dibenzodiazepinone compound, whether or not the organism naturally produces the compound. The terms apply equally to organisms in which the genetic information to produce the farnesyl dibenzodiazepinone compound is found in the organism as it exists in its natural environment, and to organisms in which the genetic information is introduced by recombinant techniques.

Specific organisms contemplated herein include, without limitation, organisms of the family Micromonosporaceae, of which preferred genera include *Micromonospora, Actinoplanes* and *Dactylosporangium;* the family Streptomycetaceae, of which preferred genera include *Streptomyces* and *Kitasatospora;* the family Pseudonocardiaceae, of which preferred genera are *Amycolatopsis* and *Saccharopolyspora;* and the family Actinosynnemataceae, of which preferred genera include *Saccharothrix* and *Actinosynnema;* however the terms are intended to encompass all organisms containing genetic information necessary to produce a farnesyl dibenzodiazepinone compound. A preferred producer of a farnesyl dibenzodiazepinone compound includes microbial strain 046-ECO11, a deposit of which was made on Mar. 7, 2003, with the International Depository Authority of Canada (IDAC), Bureau of Microbiology, Health Canada, 1015 Arlington Street, Winnipeg, Manitoba, Canada R3E 3R2, under Accession No. IDAC 070303-01.

As used herein, the term "treatment" refers to the application or administration of a therapeutic agent to a patient, or application or administration of a therapeutic agent to an isolated tissue or cell line from a patient, who has a disorder, e.g., a disease or condition, a symptom of disease, or a predisposition toward a disease, with the purpose to cure, heal, alleviate, relieve, alter, remedy, ameliorate, improve, or affect the disease, the symptoms of disease, or the predisposition toward disease.

As used herein, an "effective amount" refers

As used herein, a "pharmaceutical composition" comprises a pharmacologically effective amount of a farnesyl dibenzodiazepinone and a pharmaceutically acceptable carrier. As used herein, "pharmacologically effective amount," "therapeutically effective amount" or simply "effective amount" refers to that amount of a farnesyl dibenzodiazepinone effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

The term "pharmaceutically acceptable salt" refers to both acid addition salts and base addition salts. The nature of the salt is not critical, provided that it is pharmaceutically acceptable. Exemplary acid addition salts include, without limitation, hydrochloric, hydrobromic, hydroiodic, nitric, carbonic, sulphuric, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid and the like. Suitable pharmaceutically acceptable base addition salts include, without limitation, metallic salts made from aluminium, calcium, lithium, magnesium, potassium, sodium and zinc or organic salts made from N,N'-dibenzylethylenediamine, chloroprocaine, choline, diethanolamine, ethylenediamine, N-methylglucamine, lysine, procaine and the like. Additional examples of pharmaceutically acceptable salts are listed in *Journal of Pharmaceutical Sciences* (1977) 66:2. All of these salts may be prepared by conventional means from a farnesyl dibenzodiazepinone by treating the compound with the appropriate acid or base.

II. Farnesylated Dibenzodiazepinone Compounds

In one aspect, the invention relates to a novel farnesyl dibenzodiazepinone, referred to herein as the compound of formula II and having the chemical structure represented by the following formula:

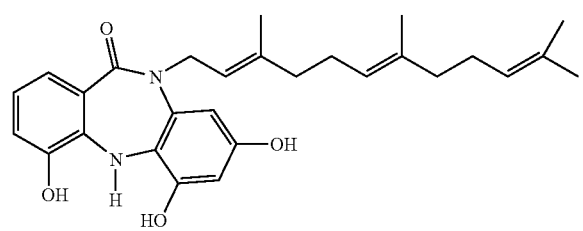

Figure 2:
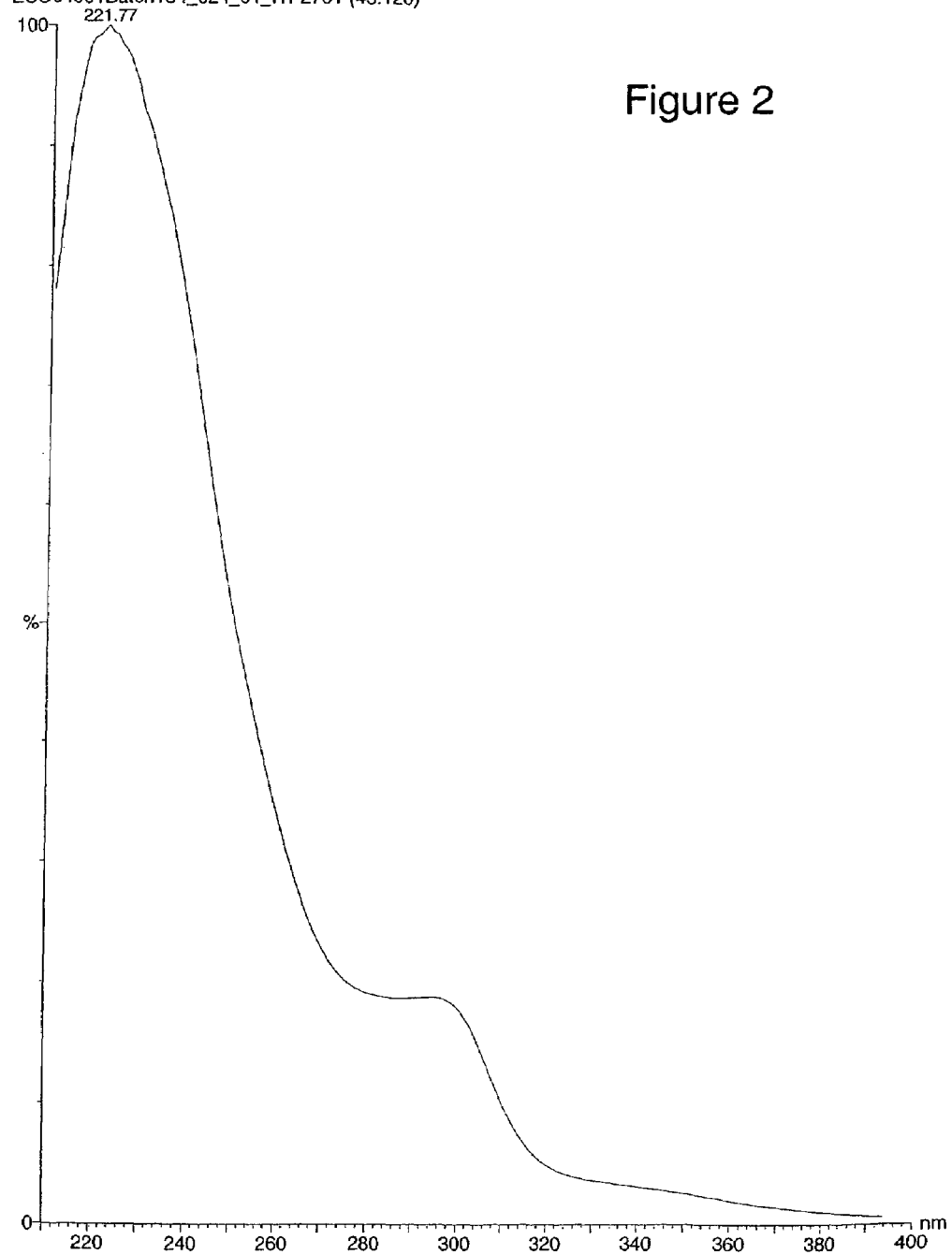
FIG. 2 shows the absorption spectrum of purified compound of Formula II with a UVmax at 230 nm and a shoulder at 290 nm.
Figure 3:
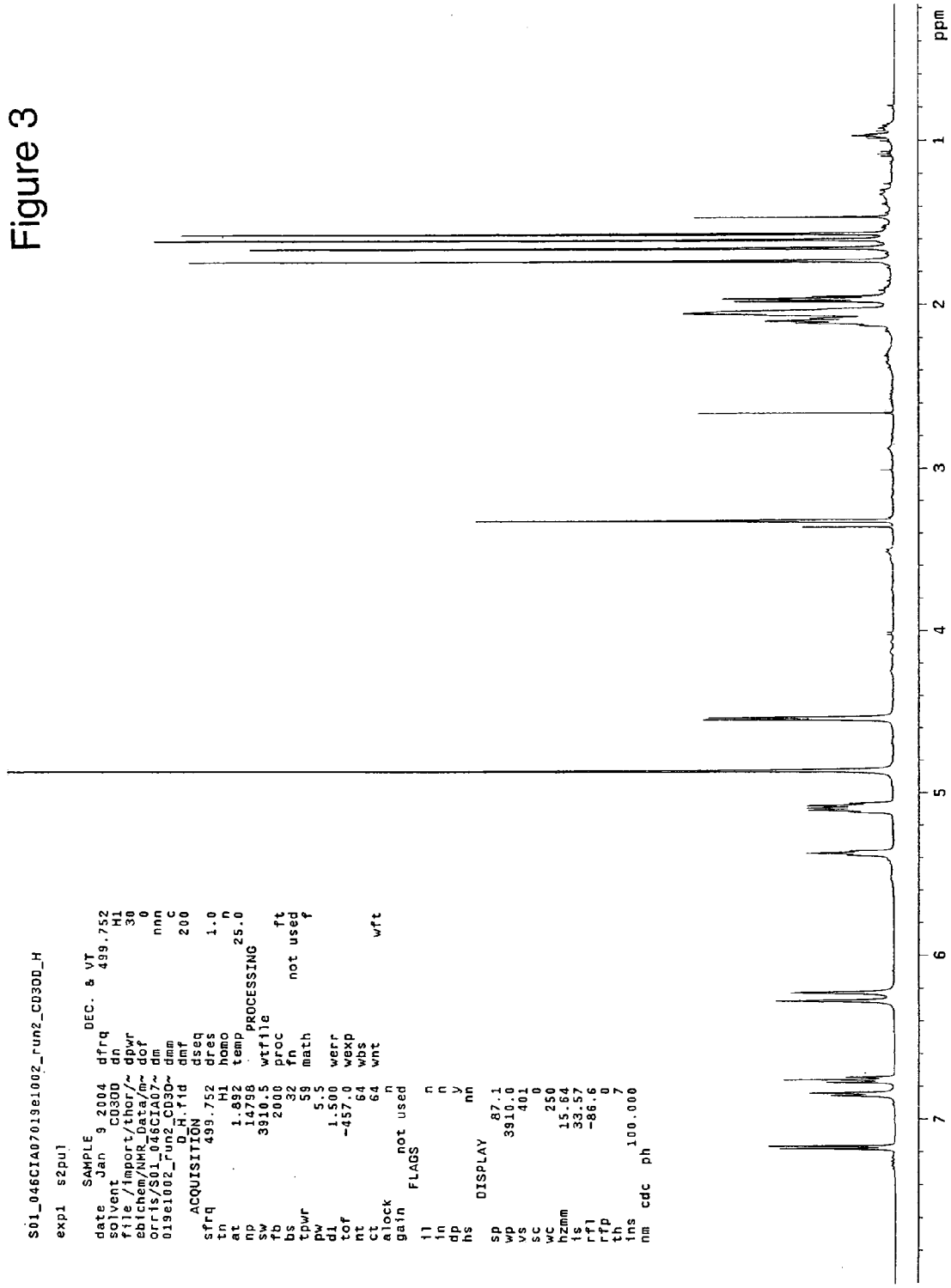
FIG. 3 shows proton NMR data for the compound dissolved in MeOH-d$_4$.
Figure 4:
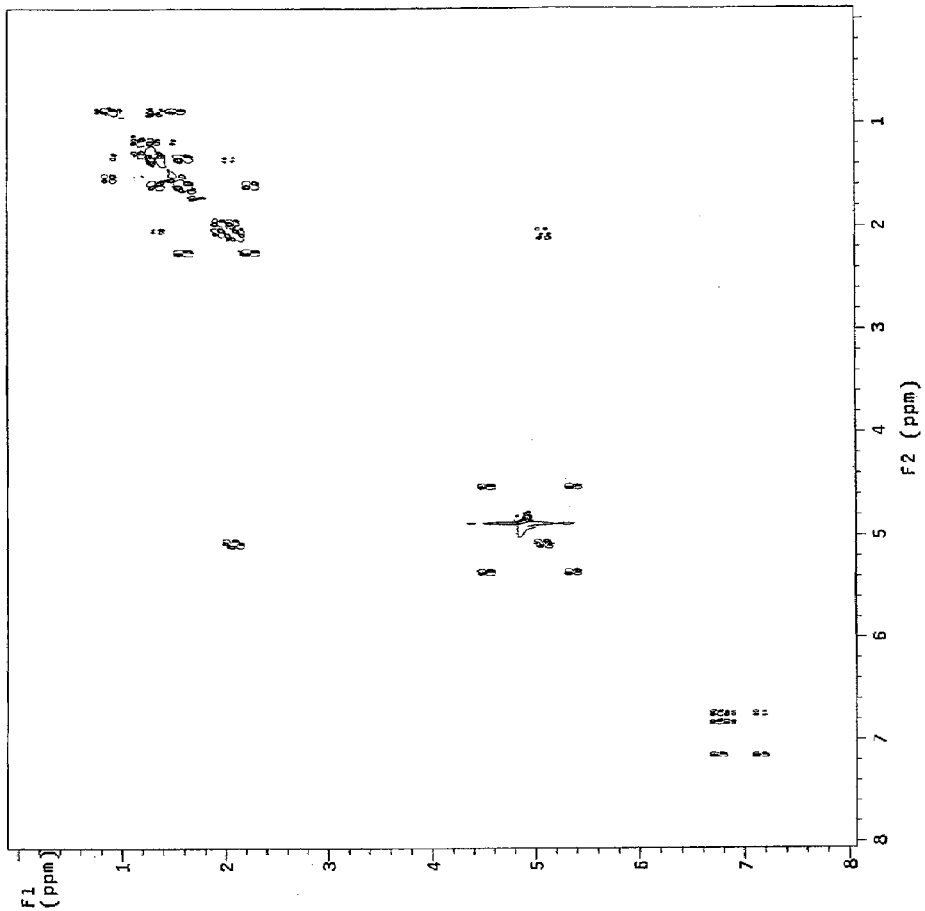
FIG. 4 shows multidimensional pulse sequences gDQ-COSY.
Figure 5:
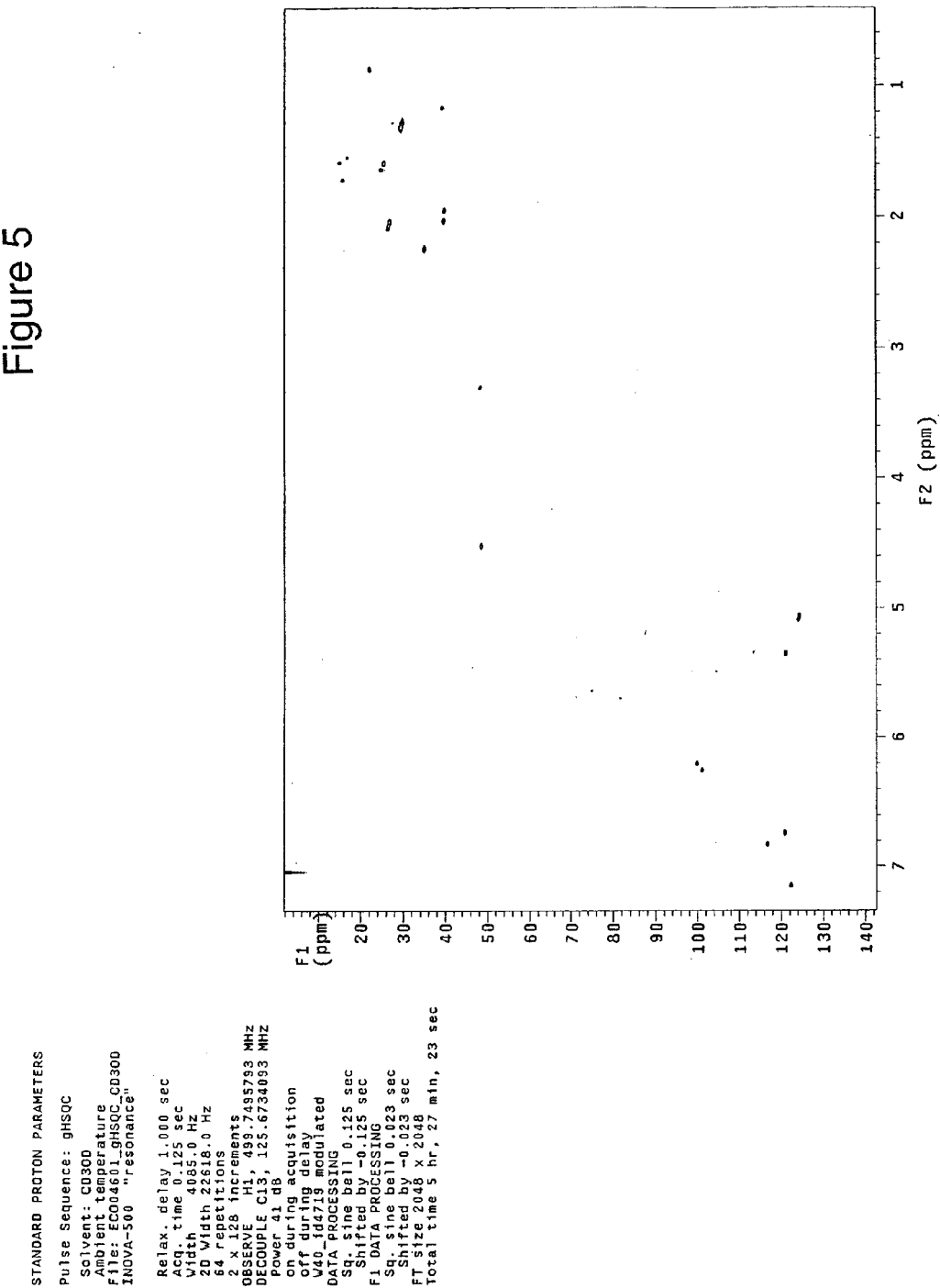
FIG. 5 shows multidimensional pulse sequences gHSQC.
Figure 6:
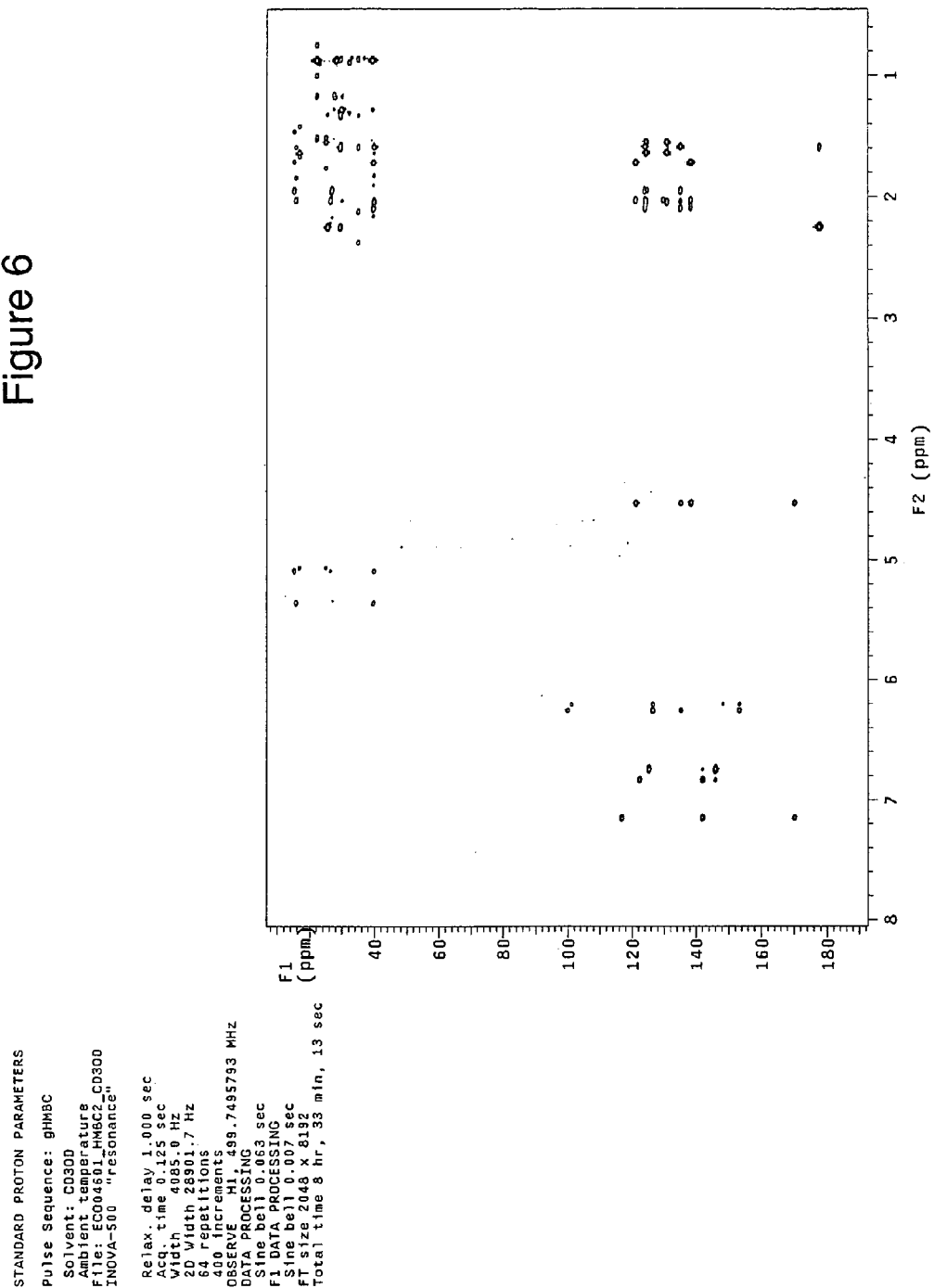
FIG. 6 shows multidimensional pulse sequences gHMBC.
Figure 7:
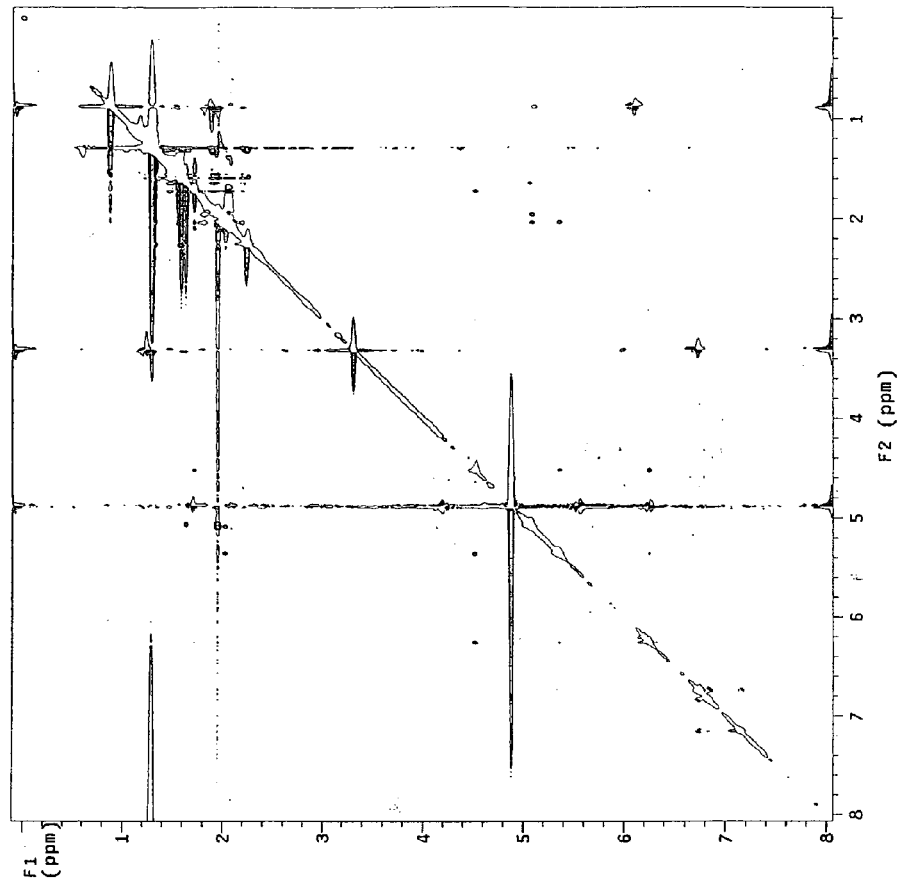
FIG. 7 shows multidimensional pulse sequences NOESY.
Figure 8:
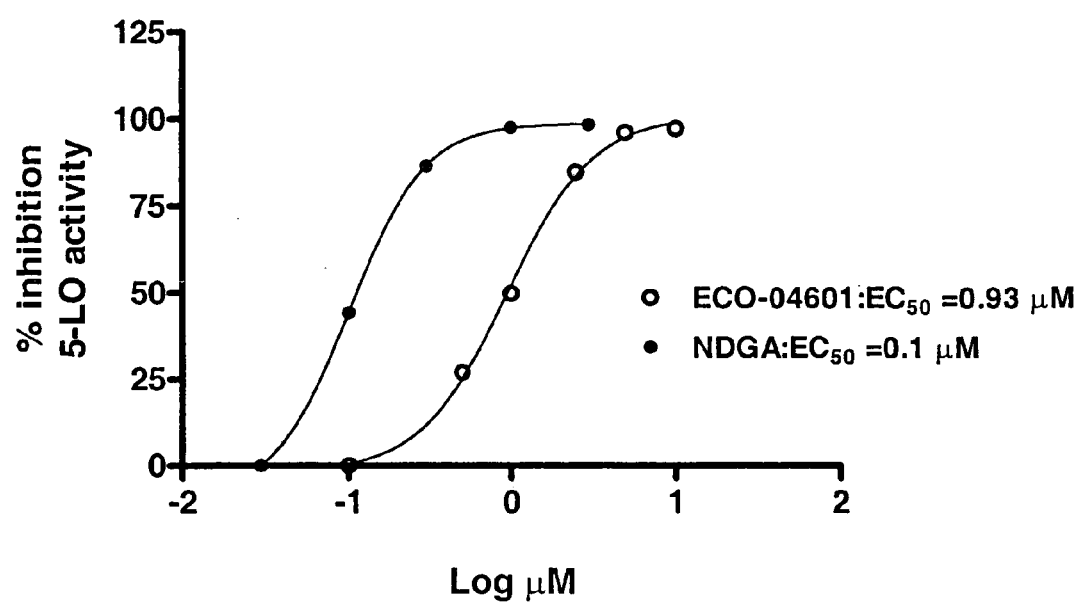
FIG. 8 shows the in vitro anti-inflammatory activity of the compound of Formula II. Graph shows percent inhibition of 5-lipoxygenase activity plotted against the Log μM concentration of the compound of Formula II and NDGA. Graph shows the EC$_{50}$ of the compound of Formula II to be 0.93 μM.

The compound of formula II may be described as a dibenzodiazepinone having a 10-farnesyl substituent located on the nitrogen atom in the 10 position of the dibenzodiazepine ring (i.e., the amide nitrogen in the diazepinone ring), and three phenolic hydroxy substituents in the 4,6 and 8 positions of the dibenzodiazepinone ring. The compound of formula II may be characterized by any one or more of its physicochemical and spectral properties given below, such as its mass, UV, and NMR spectroscopic data. Mass was determined by electrospray mass spectrometry to be 462.6 (FIG. 1); UV=230 nm with a shoulder at 290 nm (FIG. 2). NMR data were collected using MeOH-d4, including proton (FIG. 3), and multidimensional pulse sequences gDQCOSY (FIG. 4), gHSQC (FIG. 5), gHMBC (FIG. 6), and NOESY (FIG. 7).

In another aspect, the invention relates to a novel class of farnesyl dibenzodiazepinone compounds represented by Formula I:

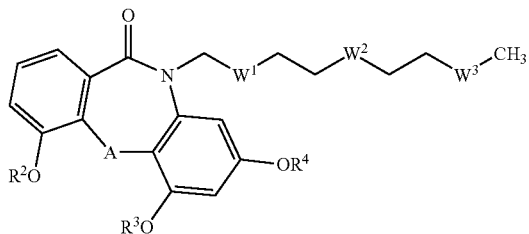

wherein,

W1, W2 and W3 is each independently selected from

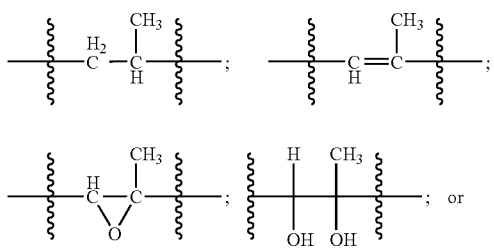

the chain from the tricycle may terminate at W3, W2 or W1 with W3, W2 or W1 respectively being either —CH=O or —CH2OH;

A is selected from —NH—, —NCH2R1, —NC(O)R1;

R1 is selected from C1–6 alkyl, C2–6 alkene, aryl or heteroaryl;

R2, R3, and R4 is each independently selected from H, R5, —C(O)R6

R5 is each independently selected from $C_{1-6}$ alkyl, $C_{2-7}$ alkalene, aryl or heteroaryl;

R6 is each independently selected from H, $C_{1-6}$ alkyl, $C_{2-7}$ alkalene, aryl or heteroaryl; or a pharmaceutically acceptable salt thereof.

In other embodiments, the invention provides compounds of Formula I, wherein A is selected from the group consisting of NH, NCH2R1, and NC(O)R1; wherein R2 is H; R3 is H; and R4 is H. In another embodiment, R2, R3 and R4 are each H; and all other groups are as previously defined. In a further embodiment, R2, R3 and R4 are each H; and W1 is —CH=CH— and all other groups are as previously defined. In a further embodiment, R2, R3 and R4 are each H, and W2 is —CH=CH— and all other groups are as previously defined. In a further embodiment, R2, R3 and R4 are each H; and W3 is —CH=CH—; and all other groups are as previously defined. In a further embodiment, A is NH; R2, R3 and R4 are each H; and all other groups are as previously defined. In a further embodiment, A is NH; each of W1, W2, and W3 is —CH=CH—; and all other groups are as previously defined. The invention encompasses all pharmaceutically acceptable salts of the foregoing compounds.

The following are exemplary compounds of the invention:

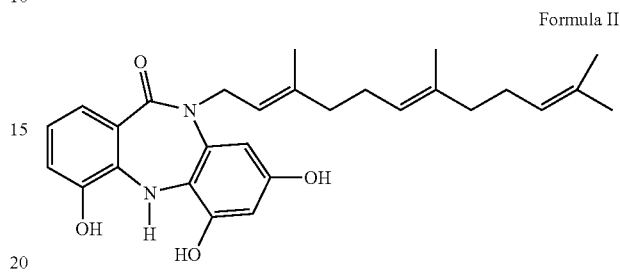

Formula II

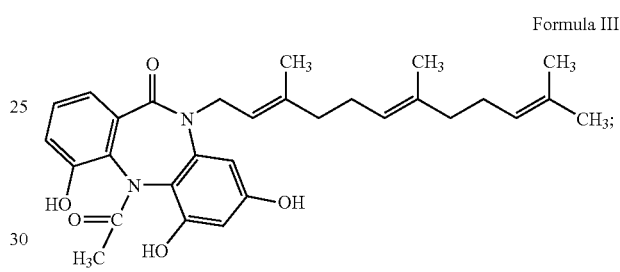

Formula III

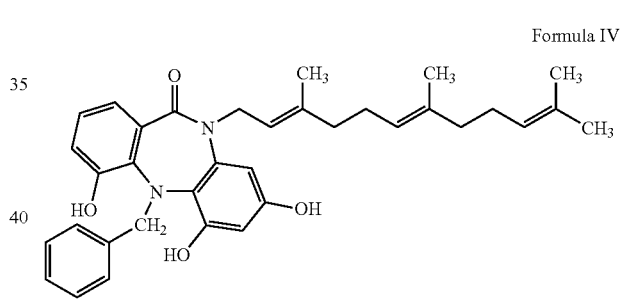

Formula IV

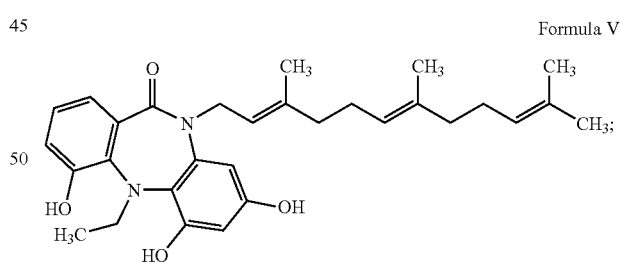

Formula V

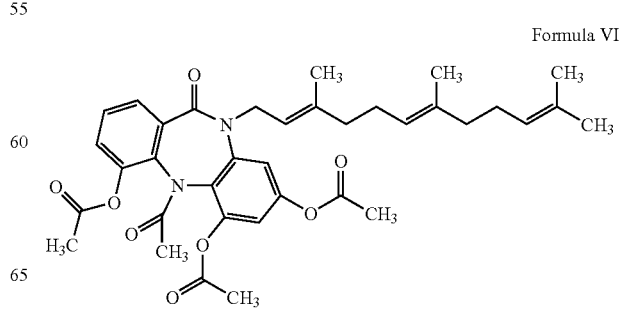

Formula VI

-continued
Formula VII
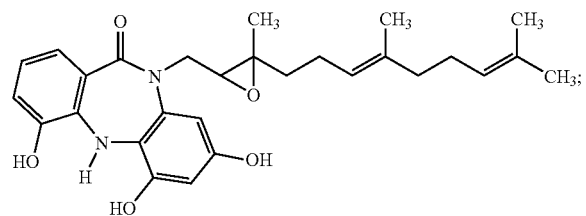
Formula XIII
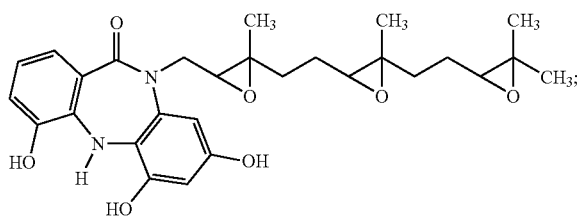
Formula VIII
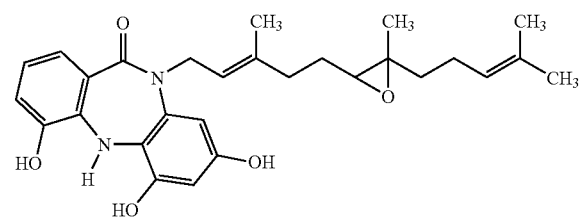
Formula XIV
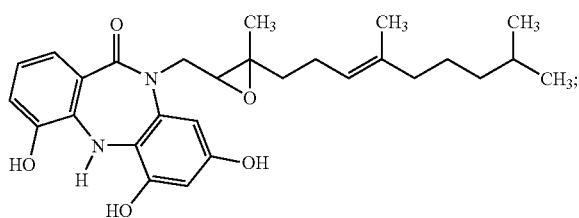
Formula VIX
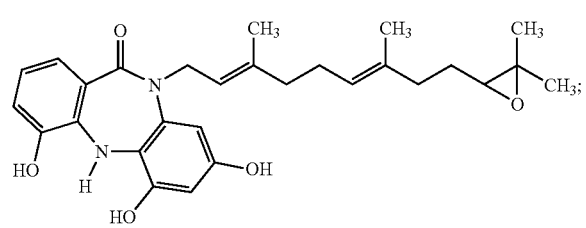
Formula XV
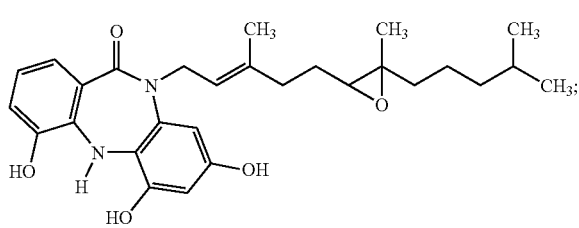
Formula X
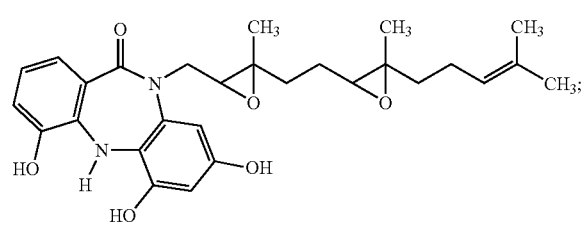
Formula XVI
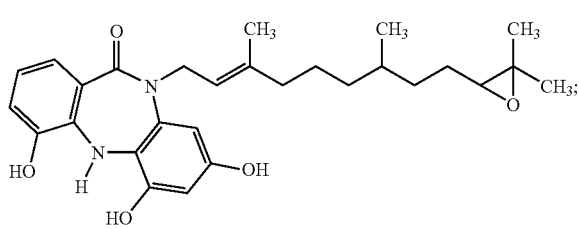
Formula XI
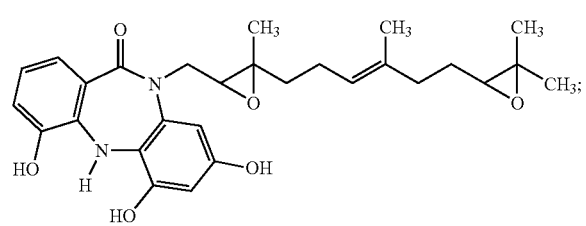
Formula XVII
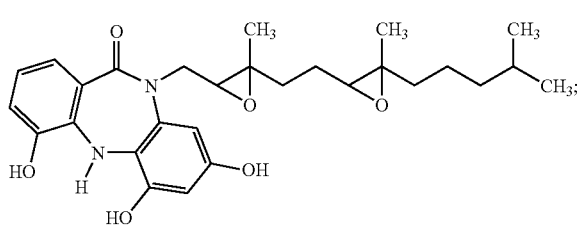
Formula XII
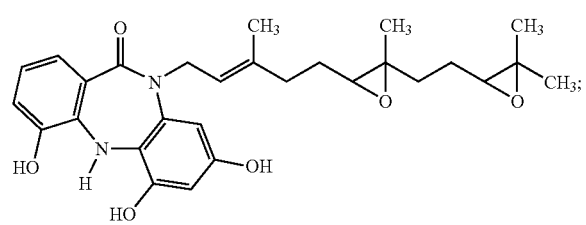
Formula XVIII
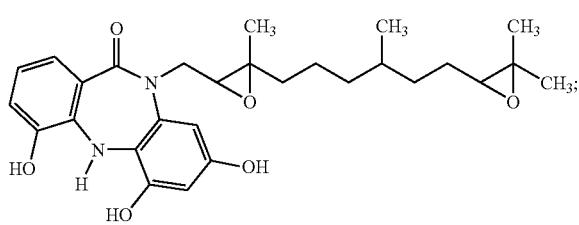

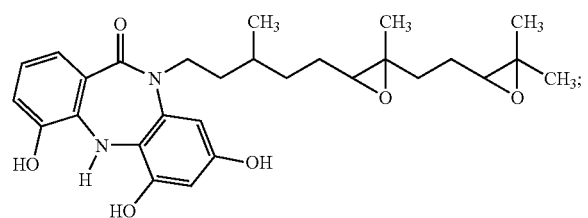
Formula XIX
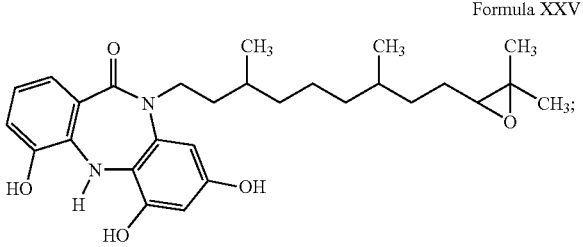
Formula XXV
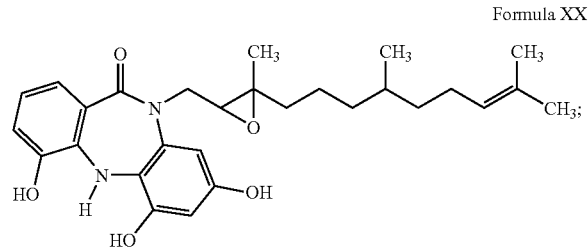
Formula XX
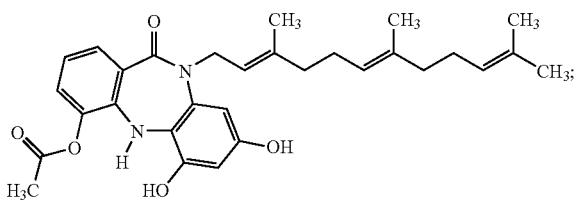
Formula XXVI
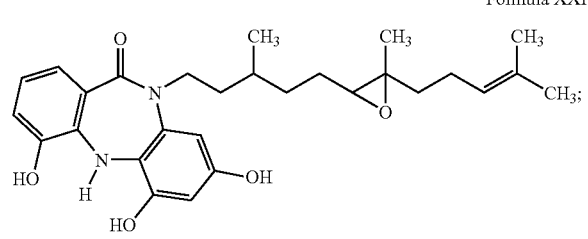
Formula XXI
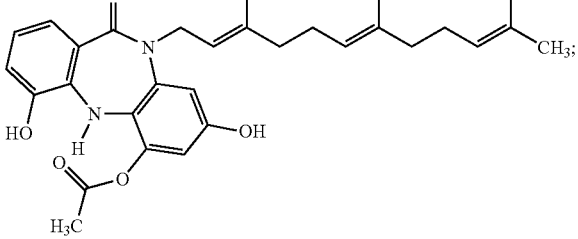
Formula XXVII
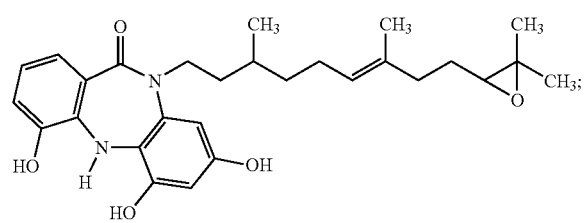
Formula XXII
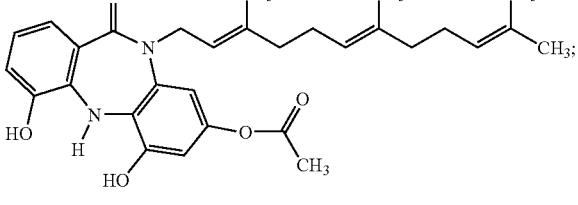
Formula XXVIII
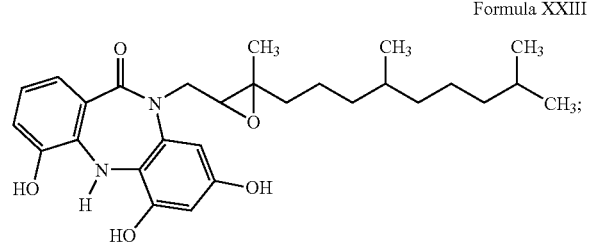
Formula XXIII
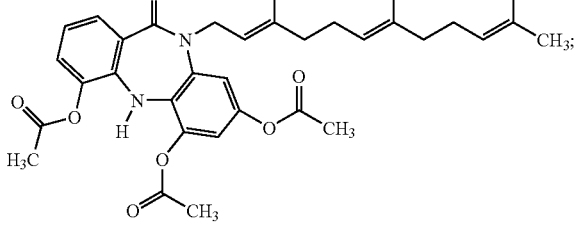
Formula XXIX
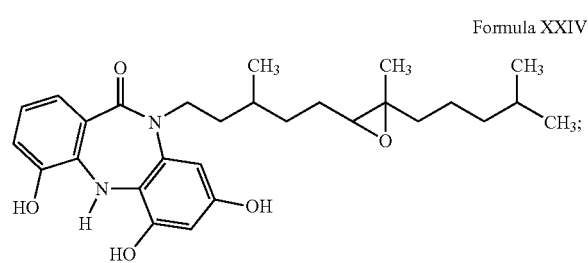
Formula XXIV
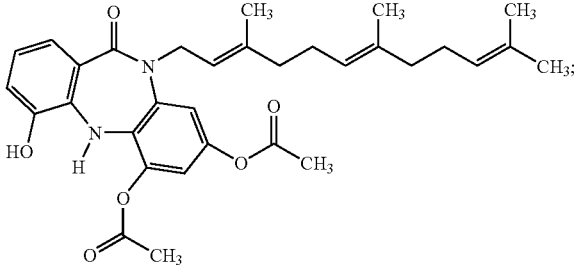
Formula XXX -continued
Formula XXXI
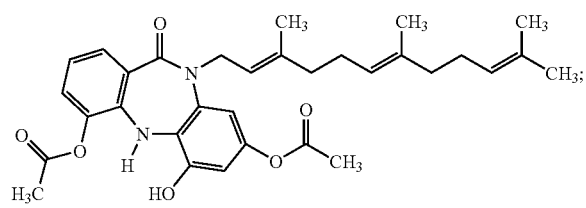
Formula XXXII
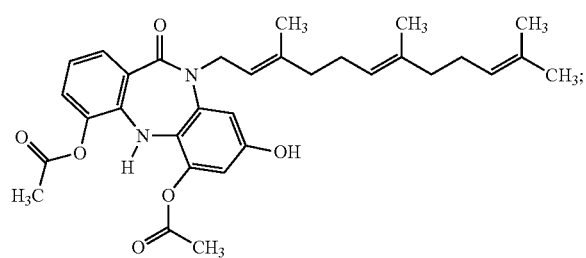
Formula XXXIII
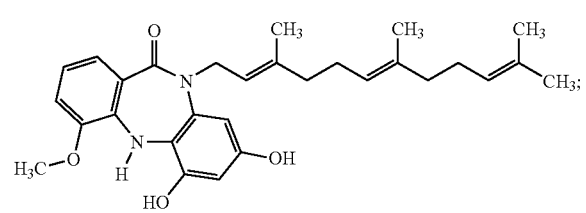
Formula XXXIV
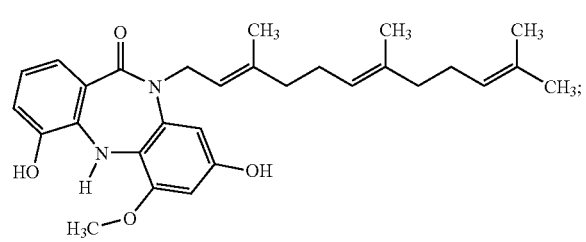
Formula XXXV
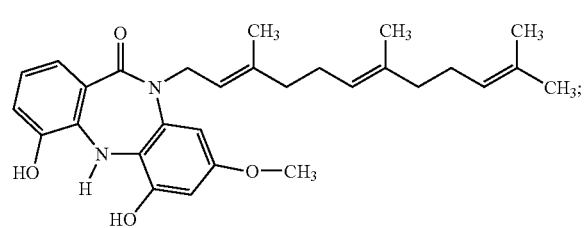
Formula XXXVI
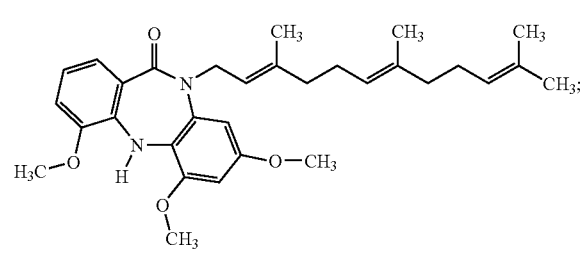
-continued
Formula XXXVII
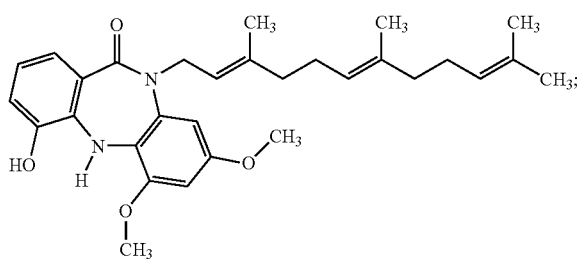
Formula XXXVIII
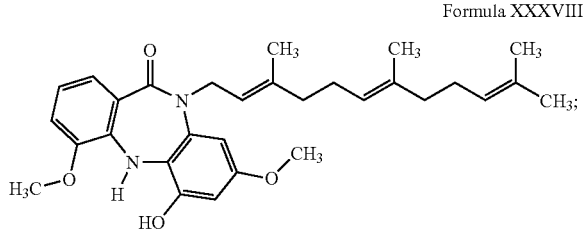
Formula XXXIX
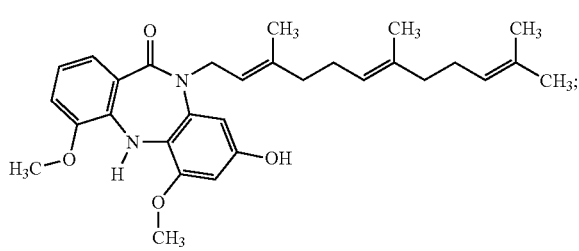
Formula XL
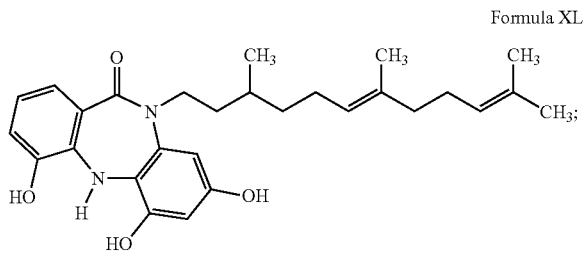
Formula XLI
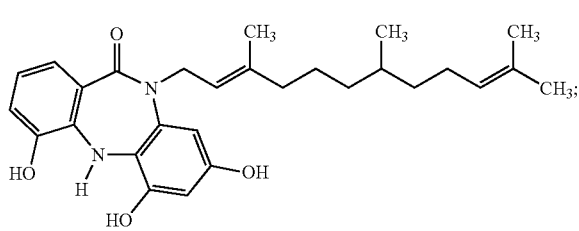
Formula XLII
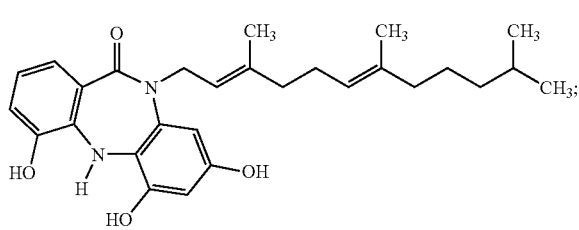

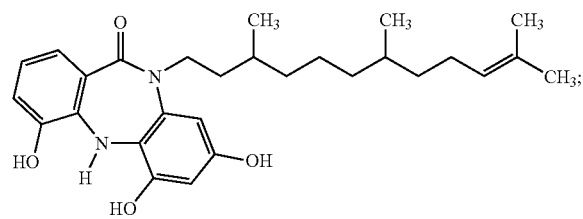
Formula XLIII
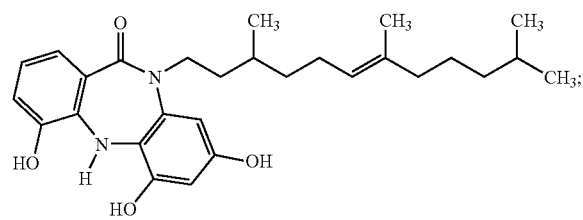
Formula XLIV
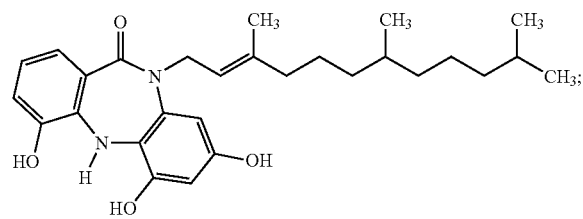
Formula XLV
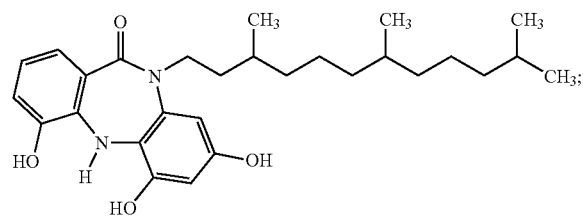
Formula XLVI
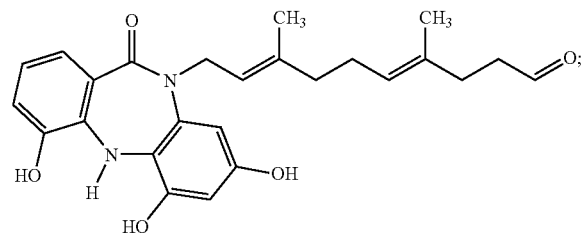
Formula XLVII
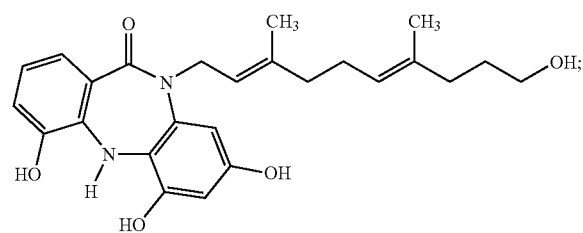
Formula XLVIII
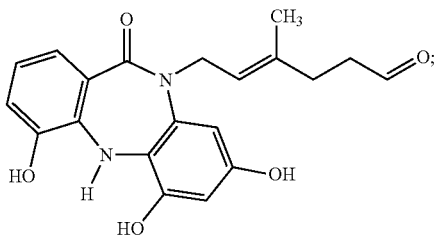
Formula XLIX
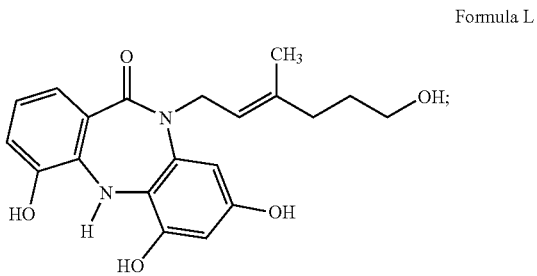
Formula L
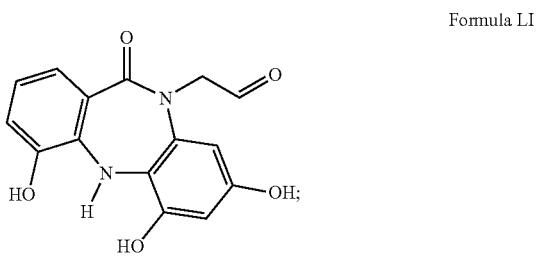
Formula LI
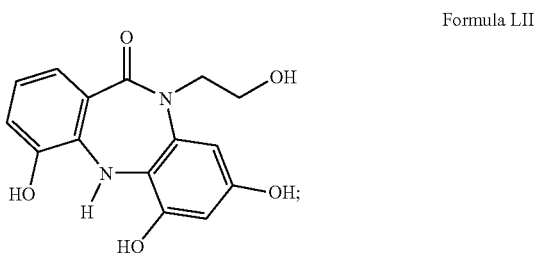
Formula LII
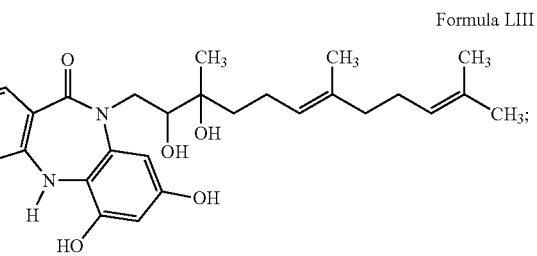
Formula LIII
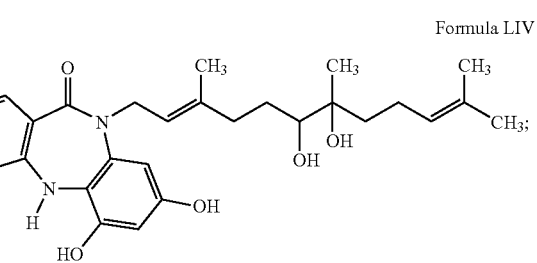
Formula LIV -continued

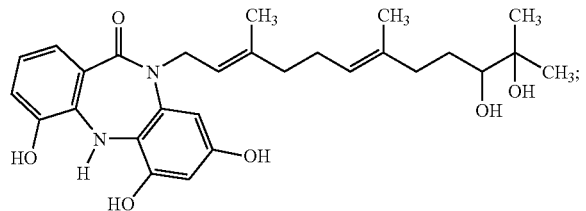

LV

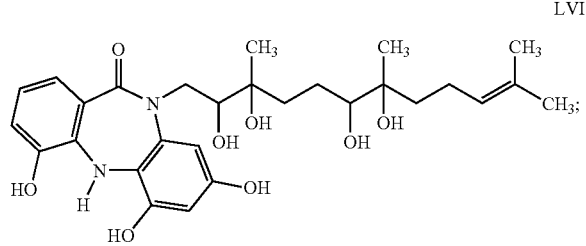

LVI

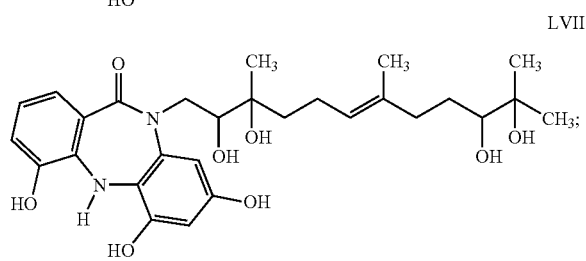

LVII

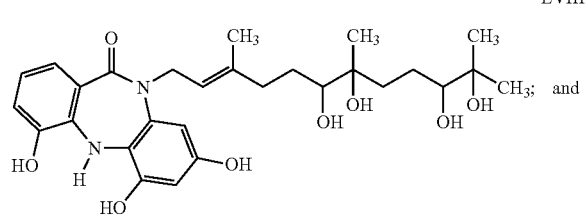

LVIII

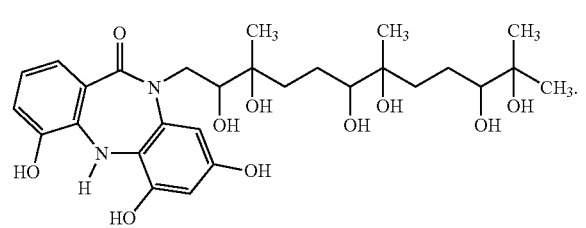

LIX

Certain embodiments expressly exclude one or more of the compounds of Formula I. In one embodiment, the compound of Formula II is excluded.

The compounds of this invention may be formulated into pharmaceutical compositions comprised of compounds of Formula I in combination with a pharmaceutical acceptable carrier, as discussed in Section V below.

III. Method of Making a Farnesyl Dibenzodiazepinone by Fermentation

In one embodiment, the compound of formula II is obtained by cultivating a novel strain of *Micromonospora*, namely *Micromonospora* sp. strain 046-ECO11. Strain 046-ECO11 was deposited on Mar. 7, 2003, with the International Depositary Authority of Canada (IDAC), Bureau of Microbiology, Health Canada, 1015 Arlington Street, Winnipeg, Manitoba, Canada R3E 3R2, under Accession No. 070303-01. The deposit of the strain was made under the terms of the Budapest Treaty on the International Recognition of the Deposit of Microorganisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112.

It is to be understood that the present invention is not limited to use of the particular strain 046-ECO11. Rather, the present invention contemplates the use of other the compound of formula II producing organisms, such as mutants or variants of 046-ECO11 that can be derived from this organism by known means such as X-ray irradiation, ultraviolet irradiation, treatment with nitrogen mustard, phage exposure, antibiotic selection and the like; or through the use of recombinant genetic engineering techniques, as described in Section IV below.

The farnesyl dibenzodiazepinone compounds of the present invention may be biosynthesized by various microorganisms. Microorganisms that may synthesize the compounds of the present invention include but are not limited to bacteria of the order Actinomycetales, also referred to as actinomycetes. Non-limiting examples of members belonging to the genera of *Actinomycetes* include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium*, and *Actinomadura*. The taxonomy of actinomycetes is complex and reference is made to Goodfellow, *Suprageneric Classification of Actinomycetes* (1989); *Bergey's Manual of Systematic Bacteriology*, Vol. 4 (Williams and Wilkins, Baltimore, pp. 2322–2339); and to Embley and Stackebrandt, "The molecular phylogeny and systematics of the actinomycetes," *Annu. Rev. Microbiol.* (1994) 48:257–289, each of which is hereby incorporated by reference in its entirety, for genera that may synthesize the compounds of the invention.

Farnesyl dibenzodiazepinone-producing microorganisms are cultivated in culture medium containing known nutritional sources for actinomycetes. Such media having assimilable sources of carbon, nitrogen, plus optional inorganic salts and other known growth factors at a pH of about 6 to about 9. Suitable media include, without limitation, the growth media provided in Table 16. Microorganisms are cultivated at incubation temperatures of about 18° C. to about 40° C. for about 3 to about 40 days.

The culture media inoculated with the farnesyl dibenzodiazepinone-producing microorganisms may be aerated by incubating the inoculated culture media with agitation, for example, shaking on a rotary shaker, or a shaking water bath. Aeration may also be achieved by the injection of air, oxygen or an appropriate gaseous mixture to the inoculated culture media during incubation. Following cultivation, the farnesyl dibenzodiazepinone compounds can be extracted and isolated from the cultivated culture media by techniques known to a skilled person in the art and/or disclosed herein, including for example centrifugation, chromatography, adsorption, filtration. For example, the cultivated culture media can be mixed with a suitable organic solvent such as n-butanol, n-butyl acetate or 4-methyl-2-pentanone, the organic layer can be separated for example, by centrifugation followed by the removal of the solvent, by evaporation to dryness or by evaporation to dryness under vacuum. The resulting residue can optionally be reconstituted with for example water, ethanol, ethyl acetate, methanol or a mixture thereof, and re-extracted with a suitable organic solvent such as hexane, carbon tetrachloride, methylene chloride or a mixture thereof. Following removal of the solvent, the compounds may be further purified by the use of standard techniques, such as chromatography.

The farnesyl dibenzodiapezinones biosynthesized by microorganisms may optionally be subjected to random and/or directed chemical modifications to form compounds that are derivatives or structural analogs. Such derivatives or structural analogs having similar functional activities are within the scope of the present invention. Farnesyl dibenzodiapezinone compounds may optionally be modified using methods known in the art and described herein.

IV. Pharmaceutical Compositions Comprising Farnesyl Dibenzodiazepinones

In another embodiment, the invention relates to a pharmaceutical composition comprising a farnesyl dibenzodiazepinone, as described in the preceding section, and a pharmaceutically acceptable carrier, as described below. The pharmaceutical composition comprising the farnesyl dibenzodiazepinone is useful for treating a variety of diseases and disorders, including cancer, inflammation and bacterial infections.

The compounds of the present invention, or pharmaceutically acceptable salts thereof, can be formulated for oral, intravenous, intramuscular, subcutaneous, topical or parenteral administration for the therapeutic or prophylactic treatment of diseases, particularly bacterial infections, acute and chronic inflammation and cancer. For oral or parental administration, compounds of the present invention can be mixed with conventional pharmaceutical carriers and excipients and used in the form of tablets, capsules, elixirs, suspensions, syrups, wafers and the like. The compositions comprising a compound of this present invention will contain from about 0.1% to about 99.9%, about 1% to about 98%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate bacterial infection, cancer or inflammation. (See, e.g., *Remington's Pharmaceutical Sciences,* Mack Publishing Company, Easton, Pa.; and Goodman and Gilman, *Pharmaceutical Basis of Therapeutics,* Pergamon Press, New York, N.Y., the contents of which are incorporated herein by reference, for a general description of the methods for administering various antimicrobial agents for human therapy). The compositions of the present invention can be delivered using controlled (e.g., capsules) or sustained release delivery systems (e.g., bioerodable matrices). Exemplary delayed release delivery systems for drug delivery that are suitable for administration of the compositions of the invention (preferably of Formula I) are described in U.S. Pat. No. 4,452,775 (issued to Kent), U.S. Pat. No. 5,239,660 (issued to Leonard), U.S. Pat. No. 3,854,480 (issued to Zaffaroni).

The pharmaceutically acceptable compositions of the present invention comprise one or more compounds of the present invention in association with one or more non-toxic, pharmaceutically acceptable carriers and/or diluents and/or adjuvants and/or excipients, collectively referred to herein as "carrier" materials, and if desired other active ingredients. The compositions may contain common carriers and excipients, such as corn starch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Tablet binders that can be included are acacia, methylcellulose, sodium carboxymethylcellulose, polyvinylpyrrolidone (Providone), hydroxypropyl methylcellulose, sucrose, starch and ethylcellulose.

Lubricants that can be used include magnesium stearate or other metallic stearates, stearic acid, silicon fluid, talc, waxes, oils and colloidal silica.

Flavouring agents such as peppermint, oil of wintergreen, cherry flavouring or the like can also be used. It may also be desirable to add a coloring agent to make the dosage form more aesthetic in appearance or to help identify the product comprising a compound of the present invention.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol (PEG), silica or talc: disintegrants, for example, potato starch, flavoring or coloring agents, or acceptable wetting agents. Oral liquid preparations generally are in the form of aqueous or oily solutions, suspensions, emulsions, syrups or elixirs and may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol (PG), sorbitol, or sorbic acid.

For intravenous (iv) use, compounds of the present invention can be dissolved or suspended in any of the commonly used intravenous fluids and administered by infusion. Intravenous fluids include, without limitation, physiological saline or Ringer's solution.

Formulations for parental administration can be in the form of aqueous or non-aqueous isotonic sterile injection solutions or suspensions. These solutions or suspensions can be prepared from sterile powders or granules having one or more of the carriers mentioned for use in the formulations for oral administration. The compounds can be dissolved in polyethylene glycol, propylene glycol, ethanol, corn oil, benzyl alcohol, sodium chloride, and/or various buffers.

For intramuscular preparations, a sterile formulation of compounds of the present invention or suitable soluble salts forming the compound, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

Alternatively, the compound of the present invention can be in powder form for reconstitution in the appropriate pharmaceutically acceptable carrier at the time of delivery. In another embodiment, the unit dosage form of the compound can be a solution of the compound or a salt thereof in a suitable diluent in sterile, hermetically sealed ampoules.

The amount of the compound of the present invention in a unit dosage comprises a therapeutically-effective amount of at least one active compound of the present invention which may vary depending on the recipient subject, route and frequency of administration. A recipient subject refers to a plant, a cell culture or an animal such as an ovine or a mammal including a human.

According to this aspect of the present invention, the novel compositions disclosed herein are placed in a pharmaceutically acceptable carrier and are delivered to a recipient subject (including a human subject) in accordance with known methods of drug delivery. In general, the methods of the invention for delivering the compositions of the invention in vivo utilize art-recognized protocols for delivering the agent with the only substantial procedural modification being the substitution of the compounds of the present invention for the drugs in the art-recognized protocols.

Likewise, the methods for using the claimed composition for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention for the agents used in the art-recognized protocols.

The compounds of the present invention provide a method for treating bacterial infections, pre-cancerous or cancerous conditions, and acute or chronic inflammatory disease. As used herein, the term "unit dosage" refers to a quantity of a therapeutically effective amount of a compound of the present invention that elicits a desired therapeutic response. As used herein, the phrase "therapeutically effective amount" means an amount of a compound of the present invention that prevents the onset, alleviates the symptoms, or stops the progression of a bacterial infection, inflammatory condition, or pre-cancerous or cancerous condition. The term "treating" is defined as administering, to a subject, a therapeutically effective amount of at least one compound of the present invention, both to prevent the occurrence of a bacterial infection, inflammation or pre-cancer or cancer condition, or to control or eliminate a bacterial infection, inflammation or pre-cancer or cancer condition. The term "desired therapeutic response" refers to treating a recipient subject with a compound of the present invention such that a bacterial or inflammatory condition or pre-cancer or cancer condition is reversed, arrested or prevented in a recipient subject.

The compounds of the present invention can be administered as a single daily dose or in multiple doses per day. The treatment regime may require administration over extended periods of time, e.g., for several days or for from two to four weeks. The amount per administered dose or the total amount administered will depend on such factors as the nature and severity of the disease condition, the age and general health of the recipient subject, the tolerance of the recipient subject to the compound and the type of the bacterial infection, inflammatory disorder, or type of cancer.

A compound according to this invention may also be administered in the diet or feed of a patient or animal. The diet for animals can be normal foodstuffs to which the compound can be added or it can be added to a premix.

The compounds of the present invention may be taken in combination, together or separately with any known clinically approved antibiotic, inflammation or anti-cancer agent to treat a recipient subject in need of such treatment.

V. Method of Inhibiting Tumor Growth

In another embodiment, the present invention relates to a method of inhibiting tumor growth. Compounds as described herein can possess antitumor activity. The compounds are effective against mammalian tumor cells such as leukemia cells, melanoma cells, breast carcinoma cells, lung carcinoma cells, pancreatic carcinoma cells, ovarian carcinoma cells, renal carcinoma cells, colon carcinoma cells prostate carcinoma cells and glioma cells. The antitumor method of the invention results in inhibition of tumor cells. The term "inhibition", when used in conjunction with the antitumor method refers to suppression, killing, stasis, or destruction of tumor cells. The antitumor method preferably results in prevention, reduction or elimination of invasive activity and related metastasis of tumor cells. The term "effective amount" when used in conjunction with the antitumor cell method refers to the amount of the compound sufficient to result in the inhibition of mammalian tumor cells.

The inhibition of mammalian tumor growth according to this method can be monitored in several ways. First, tumor cells grown in vitro can be treated with the compound and monitored for growth or death relative to the same cells cultured in the absence of the compound. A cessation of growth or a slowing of the growth rate (i.e., the doubling rate), e.g., by 10% or more, is indicative of tumor cell inhibition. Alternatively, tumor cell inhibition can be monitored by administering the compound to an animal model of the tumor of interest. Examples of experimental animal tumor models are known in the art and described in the examples herein. A cessation of tumor growth (i.e., no further increase in size) or a reduction in tumor size (i.e., tumor volume) or cell number (e.g., at least a 10% decrease in either) in animals treated with a compound as described herein relative to tumors in control animals not treated with the compound is indicative of tumor growth inhibition.

To monitor the efficacy of tumor treatment in a human, tumor size or tumor cell titer is measured before and after initiation of the treatment, and treatment is considered effective if either the tumor size or titer ceases further growth, or if the tumor is reduced in size or titer, e.g., by at least 10% or more (e.g., 20%, 30%, 40%, 50%, 60%, 70%, 80%, 90% or even 100%, that is, the absence of the tumor). Methods of determining the size or cell titer of a tumor in vivo vary with the type of tumor, and include, for example, various imaging techniques well known to those in the medical imaging or oncology fields (MRI, CAT, PET, etc.), as well as histological techniques and flow cytometry.

For the antitumor method of the invention, a typical effective dose of the compounds given orally or parenterally would be from about 5 to about 100 mg/kg of body weight of the subject with a daily dose ranging from about 15 to about 300 mg/kg of body weight of the subject.

VI. Method of Treating Cancer

In another embodiment, the present invention relates to a method of treating a precancerous or cancerous condition in a mammal, comprising the steps of administrating a pharmaceutical composition, containing a dibenzodiazepinone compound of the present invention in combination with a physiologically acceptable carrier. In one embodiment, the compound is represented by Formula II. As described elsewhere in the application, the compounds of the present invention can have antitumor activity. Specifically, the compounds are effective against mammalian tumor cells such as leukemia cells, melanoma cells, breast carcinoma cells, lung carcinoma cells, pancreatic carcinoma cells, ovarian carcinoma cells, renal carcinoma cells, colon carcinoma cells, prostate carcinoma cells and glioma cells.

In addition, the compound of Formula II is bioavailable via the oral, intraperitoneal, subcutaneous and intravenous administration. Furthermore, as is described within the Examples section, the compounds of the present invention penetrate into brain tissues, and therefore can be useful in the treatment of numerous pre-cancerous and cancerous conditions of the brain.

The cancer treatment method preferably results in prevention, reduction or elimination of invasive activity and related metastasis of tumor cells. The term "therapeutically effective amount" when used in conjunction with the cancer treatment method refers to the amount of the compound sufficient to result in the prevention, reduction or elimination tumors or cancer in a mammal.

The treatment of cancer according to this method can be monitored in several ways. To monitor the efficacy of tumor treatment in a human, tumor size or tumor cell titer is measured before and after initiation of the treatment, and treatment is considered effective if either the tumor size or titer ceases further growth, or if the tumor is reduced in size or titer, e.g., by at least 10% or more (e.g., 20%, 30%, 40%, 50%, 60%, 70%, 80%, 90% or even 100%, that is, the absence of the tumor). Methods of determining the size or cell titer of a tumor in vivo vary with the type of tumor, and include, for example, various imaging techniques well known to those in the medical imaging or oncology fields (MRI, CAT, PET, etc.), as well as histological techniques and flow cytometry.

For the cancer treatment method of the invention, a typical effective dose of the compounds given orally or parenterally would be from about 5 to about 100 mg/kg of body weight of the subject with a daily dose ranging from about 15 to about 300 mg/kg of body weight of the subject. Alternatively, compounds can be given intravenously, intraperitoneally or subcutaneously at a range from about 5 to about 300 mg/kg.

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable salt, ester, salt of an ester or other derivative of a compound of this invention which, upon administration to a recipient, is capable of providing, either directly or indirectly, a compound of this invention or an inhibitorily active metabolite or residue thereof. Particularly favored derivatives or prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Unless otherwise indicated, all numbers expressing quantities of ingredients, properties such as molecular weight, reaction conditions, $IC_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Preparation of Production Culture

Unless otherwise noted, all reagents were purchased from Sigma Chemical Co. (St. Louis, Mo.), (Aldrich). *Micromonospora* spp. (deposit accession number IDAC 070303-01) was maintained on agar plates of ISP2 agar (Difco Laboratories, Detroit, Mich.). An inoculum for the production phase was prepared by transferring the surface growth of the *Micromonospora* spp. from the agar plates to 125-mL flasks containing 25 mL of sterile medium comprised of 24 g potato dextrin, 3 g beef extract, 5 g Bacto-casitone, 5 g glucose, 5 g yeast extract, and 4 g $CaCO_3$ made up to one liter with distilled water (pH 7.0). The culture was incubated at about 28° C. for approximately 60 hours on a rotary shaker set at 250 rpm. Following incubation, 10 mL of culture was transferred to a 2 L baffled flask containing 500 mL of sterile production medium containing 20 g/L potato dextrin, 20 g/L glycerol, 10 g/L Fish meal, 5 g/L Bacto-peptone, 2 g/L $CaCO_3$, and 2 g/L $(NH_4)_2SO_4$, pH 7.0.

Fermentation broth was prepared by incubating the production culture at 28° C. in a rotary shaker set at 250 rpm for one week.

Example 2

Isolation 500 mL ethyl acetate was added to 500 mL of fermentation broth prepared as described in Example 1 above. The mixture was agitated for 30 minutes on an orbital shaker at 200 rpm to create an emulsion. The phases were separated by centrifugation and decantation. Between 4 and 5 g of anhydrous $MgSO_4$ was added to the organic phase, which was then filtered and the solvents removed in vacuo.

An ethyl acetate extract from 2 L fermentation was mixed with HP-20 resin (100 mL; Mitsubishi Casei Corp., Tokyo, Japan) in water (300 mL). Ethyl acetate was removed in vacuo, the resin was filtered on a Buchner funnel and the filtrate was discarded. The adsorbed HP-20 resin was then washed successively with 2×125 mL of 50% acetonitrile in water, 2×125 mL of 75% acetonitrile in water and 2×125 mL of acetonitrile.

Fractions containing the compound of Formula II were evaporated to dryness and 100 mg was digested in the 5 mL of the upper phase of a mixture prepared from chloroform, cyclohexane, methanol, and water in the ratios, by volume, of 5:2:10:5. The sample was subjected to centrifugal partition chromatography using a High Speed Countercurrent (HSCC) system (Kromaton Technologies, Angers, France) fitted with a 200 mL cartridge and prepacked with the upper phase of this two-phase system. The HSCC was run with the lower phase mobile and the compound of Formula II was eluted at approximately one-half column volume. Fractions were collected and the compound of Formula II was detected by TLC of aliquots of the fractions on commercial Kieselgel $60F_{254}$ plates. Compound could be visualized by inspection of dried plates under UV light or by spraying the plates with a spray containing vanillin (0.75%) and concentrated sulfuric acid (1.5%, v/v) in ethanol and subsequently heating the plate. Fractions contained substantially pure compound of Formula II, although highly colored. A buff-colored sample could be obtained by chromatography on HPLC as follows.

6 mg of sample was dissolved in acetonitrile and injected onto a preparative HPLC column (XTerra ODS (10 μm), 19×150 mm, Waters Co., Milford, Mass.), with a 9 mL/min flow rate and UV peak detection at 300 nm. The column was eluted with acetonitrile/buffer (20 mM of $NH_4HCO_3$) according to the following gradient shown in Table 1

TABLE 1

| Time (min) | Water (%) | Acetonitrile (%) |
| --- | --- | --- |
| 0 | 70 | 30 |
| 10 | 5 | 95 |
| 15 | 5 | 95 |
| 20 | 70 | 30 |

Fractions containing the compound of Formula II eluted at approximately 11:0 min and were combined, concentrated and lyophilized to give a yield of 3.8 mg compound.

Alternative Protocol 1

The compound of Formula II was also isolated using the following alternative protocol. At the end of the incubation period, the fermentation broth from the baffled flasks of Example 1 was centrifuged and the supernatant decanted from the pellet containing the bacterial mycelia. 100 mL of 100% MeOH was added to the mycelial pellet and the sample was stirred for 10 minutes and centrifuged for 15 minutes. The methanolic supernatant was decanted and saved. 100 mL of acetone was then added to the mycelial pellet and stirred for 10 minutes then centrifuged for 15 minutes. The acetonic supernatant was decanted and combined with the methanolic supernatant. Finally, 100 mL of 20% MeOH/$H_2O$ was added to the mycelial pellet, stirred for 10 minutes and centrifuged for 15 minutes. The supernatant was combined with the acetonic and methanolic supernatants.

The combined supernatant was added to 400 ml of HP-20 resin in 1000 mL of water and the organics were removed in vacuo. The resulting slurry was filtered on a Buchner funnel and the filtrate was discarded. Adsorbed HP-20 resin was washed successively with 2×500 mL of 50% MeOH/$H_2O$, 2×500 mL of 75% MeOH/$H_2O$ and 2×500 mL of MeOH.

The individual washes were collected separately and analyzed by TLC as described above. Those fractions containing the compound of Formula II were evaporated to near dryness and lyophilized. The lyophilizate was dissolved in methanol and injected onto a preparative HPLC column (Xterra ODS (10 μm), 19×150 mm, Waters Co., Milford, Mass.) with a flow rate of 9 mL/min and peak detection at 300 nm.

The column was eluted with acetonitrile/buffer (5 mM of $NH_4HCO_3$) according to gradient shown in Table 2.

TABLE 2

| Time (min) | Buffer (%) | Acetonitrile (%) |
| --- | --- | --- |
| 0 | 95 | 5 |
| 15 | 45 | 55 |
| 20 | 5 | 95 |
| 30 | 5 | 95 |
| 35 | 95 | 5 |

Fractions containing the compound of Formula II were combined, concentrated and lyophilized to yield about 33.7 mg of compound.

Alternative Protocol 2

10 liters of the whole broth from Example 1 are extracted twice with equal volumes of ethyl acetate and the two extracts are combined and concentrated to dryness. The dried extract is weighed, and for every gram of dry extract, 100 mL of MeOH—$H_2O$ (2:1 v/v) and 100 mL of hexane is added. The mixture is swirled gently but well to achieve dissolution. The two layers are separated and the aqueous layer is washed with 100 mL of hexane. The two hexane layers are combined and the combined hexane solution is washed with 100 mL methanol:water (2:1, v/v). The two methanol:water layers are combined and treated with 200 mL of EtOAc and 400 mL of water. The layers are separated and the aqueous layer is extracted twice more with 200 mL portions of EtOAc. The EtOAc layers are combined and concentrated. The residue obtained will be suitable for final purification, either by HSCC or by HPLC as described above. This extraction process achieves a ten-fold purification when compared with the extraction protocol used above.

Example 3

Elucidation of the Structure of Compound of Formula II

The structure of the compound of Formula II was derived from spectroscopic data, including mass, UV, and NMR spectroscopy. Mass was determined by electrospray mass spectrometry to be 462.6 (FIG. 1), UVmax 230 nm with a shoulder at 290 nm (FIG. 2). NMR data were collected dissolved in MeOH-d4 including proton (FIG. 3), and multidimensional pulse sequences gDQCOSY (FIG. 4), gHSQC (FIG. 5), gHMBC (FIG. 6), and NOESY (FIG. 7).

A number of cross peaks in the 2D spectra of the compound of Formula II are key in the structural determination. For example, the farnesyl chain is placed on the amide nitrogen by a strong cross peak between the proton signal of the terminal methylene of that chain at 4.52 ppm and the amide carbonyl carbon at 170 ppm in the gHMBC experiment. This conclusion is confirmed by a cross peak in the NOESY spectrum between the same methylene signals at 4.52 ppm and the aromatic proton signal at 6.25 ppm from one of the two protons of the tetra substituted benzenoid ring.

Based on the mass, UV and NMR spectroscopy data, the structure of the compound was determined to be the structure of Formula II.

Example 4

Anticancer Activity In Vitro Against Human and Animal Tumor Cell Lines from Various Tissues Culture conditions: The cell lines listed in Table 3 were used to characterize the cytotoxicity of the compound of Formula II against human and animal tumor cell lines. These cell lines were shown to be free of mycoplasma infection and were maintained on the appropriate media (Table 3) supplemented with 10% heat-inactivated fetal bovine serum and 1% penicillin-streptomycin, under 5% $CO_2$ at 37° C. Cells were passaged twice to three times per week. Viability was examined by staining with 0.25% trypan blue and only flasks where cell viability was >95% were used for this study.

Cell lines amplification and plating: Tumor cells were seeded ($1-3\times10^3$ cells per 100 μL) in 96-wells flat bottom microtiter plates and incubated at 37° C. and 5% $CO_2$ for 16 hrs before treatment in drug-free medium supplemented with 10% serum.

Evaluation of inhibitory activity on cell proliferation: Cells were incubated for 96 hrs with 6 $log_{10}$-fold concentrations of the test substance starting at 10 μg/ml (20 μM). The test substance stock solution (5 mg/mL) was initially diluted at 1/70 fold in medium supplemented with serum. Other concentrations were then obtained from 1/10 fold successive dilutions in the same supplemented medium. Cell survival was evaluated 96 h later by replacing the culture media with 150 μL fresh medium containing 10 mM 4-(2-hydroxyethyl)-1-piperazineethanesulfonic acid buffer, pH 7.4. Next, 50 μL of 2.5 mg/mL of 3-(4,5-dimethylthiazo-2-yl)-2,5-diphenyltetrazolium bromide (MTT) in phosphate buffer solution, pH 7.4, was added. After 34 h of incubation at 37° C, the medium and soluble MTT was removed, and 200 μL of dimethylsulfoxide was added to dissolve the precipitate of reduced MTT followed by addition of 25 μL glycine buffer (0.1 M glycine plus 0.1 M NaCl, pH 10.5). The absorbance was determined at 570 nm with a microplate reader. Results were expressed as the concentration of drug which inhibits 50% of the cell growth ($IC_{50}$). The $IC_{50}$ values shown in Table 3 demonstrated a pharmacologically relevant cytotoxic activity of the compound of Formula II against a variety of tumor types such as leukemias, melanomas, pancreatic and breast carcinomas.

TABLE 3

| Cell lines | Type | Origin | Source | Culture medium | $IC_{50}$ ($\times10^{-6}$ M) |
| --- | --- | --- | --- | --- | --- |
| K562 | Leukemia myelogeneous | Human | ATCC | RPMI 1640 | 8.6 |
| P388 | Leukemia | Mouse | ATCC | RPMI 1640 | 10.9 |
| I83 | Leukemia | Human | ATCC | RPMI 1640 | 2.7 |
| B16 (F10) | Melanoma | Mouse | ATCC | RPMI 1640 | 11.4 |
| SK-MEL 28 | Melanoma | Human | ATCC | RPMI 1640 | 14.0 |
| SK-MEL 28$^{VEGF}$ | Melanoma (expressing VEGF) | Human | ATCC | RPMI 1640 | 14.3 |
| SK-MEL-1 | Melanoma | Human | ATCC | EMEM 1% non-essential amino acid 1% Sodium puryvate | 14.1 |
| Panc 96 | Pancreatic carcinoma | Human | ATCC | RPMI 1% Sodium puryvate | 12.5 |
| Panc 10.05 | Pancreatic carcinoma | Human | ATCC | RPMI 1% Sodium puryvate Insulin | 14.2 |
| MCF-7 | Breast adenocarcinoma | Human | ATCC | RPMI 1640 | 9.7 |

Example 5

Anticancer Activity In Vitro Against Various Human Tumor Cell Lines from the U.S. National Cancer Institute Panel A study measuring the in vitro antitumor activity of the compound of Formula II was performed by the National Cancer Institute (National Institutes of Health, Bethesda, Md., USA) against panel of human cancer cell lines in order to determine the compound of Formula II concentrations needed to obtain a 50% inhibition of cell proliferation ($GI_{50}$). The operation of this unique screen utilizes 50 different human tumor cell lines, representing leukemia, melanoma and cancers of the lung, colon, brain, ovary, breast, prostate, and kidney.

Culture conditions and plating: The human tumor cell lines of the cancer-screening panel were grown in RPMI 1640 medium containing 5% fetal bovine serum and 2 mM L-glutamine. For a typical screening experiment, cells were inoculated into 96 well microtiter plates in 100 μL at plating densities ranging from 5,000 to 40,000 cells/well depending on the doubling time of individual cell lines (Table 4). After cell inoculation, the microtiter plates were incubated at 37° C., 5% $CO_2$, 95% air and 100% relative humidity for 24 h prior to addition of experimental drugs. After 24 h, two plates of each cell line were fixed in situ with TCA, to represent a measurement of the cell population for each cell line at the time of drug addition (Tz).

Evaluation of inhibitory activity on cell proliferation: The compound of Formula II was provided as a lyophilized powder with an estimated purity of 90+%. The compound was stored at −20° C. until day of use. The compound of Formula II was solubilized in dimethyl sulfoxide at 400-fold the desired final maximum test concentration. At the time of drug addition, an aliquot of frozen concentrate was thawed and diluted to twice the desired final maximum test concentration with complete medium containing 50 μg/mL gentamicin. Additional four, 10-fold or ½ log serial dilutions were made to provide a total of five drug concentrations plus control. Aliquots of 100 μl of these different drug dilutions were added to the appropriate microtiter wells already containing 100 μl of medium, resulting in the required final drug concentrations ($8.0 \times 10^{-5}$ M to $8.0 \times 10^{-9}$ M).

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. Supernatants were discarded, and the plates were washed five times with tap water and air-dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air-dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA).

The growth inhibitory activity of the compound of Formula II was measured by NCI utilizing the $GI_{50}$ value, rather than the classical $IC_{50}$ value. The $GI_{50}$ value emphasizes the correction for the cell count at time zero and, using the seven absorbance measurements [time zero, (Tz), control growth, (C), and test growth in the presence of drug at the five concentration levels (Ti)], $GI_{50}$ is calculated as $[(Ti-Tz)/(C-Tz)] \times 100 = -50$, which is the drug concentration resulting in a 50% reduction in the net protein increase (as measured by SRB staining) in control cells during the drug incubation.

Result: The compound of Formula II shows a significant antitumor activity against several types of tumor as revealed by the NCI screening. Results of the screen are shown in Table 4, and more detailed results of activity against gliomas are shown in Example 5 (Table 5).

TABLE 4

| Cell Line Name | Type | Origin | Inoculation Density (number of cells/well) | $GI_{50}$ ($\times 10^{-6}$ M) |
|---|---|---|---|---|
| CCRF-CEM | Leukemia | Human | 40,000 | 1.08 |
| K-562 | Leukemia | Human | 5,000 | 1.43 |
| RPMI-8226 | Leukemia | Human | 20,000 | 3.15 |
| A549/ATCC | Non-Small Cell Lung | Human | 7,500 | 9.10 |
| EKVX | Non-Small Cell Lung | Human | 20,000 | 0.23 |
| HOP-62 | Non-Small Cell Lung | Human | 10,000 | 8.29 |
| NCI-H226 | Non-Small Cell Lung | Human | 20,000 | 2.00 |
| NCI-H23 | Non-Small Cell Lung | Human | 20,000 | 2.02 |
| NCI-H460 | Non-Small Cell Lung | Human | 7,500 | 13.60 |
| NCI-H522 | Non-Small Cell Lung | Human | 20,000 | 3.44 |
| COLO 205 | Colon | Human | 15,000 | 12.70 |
| HCT-116 | Colon | Human | 5,000 | 2.92 |
| HCT-15 | Colon | Human | 10,000 | 9.73 |
| HT29 | Colon | Human | 5,000 | 20.70 |
| SW-620 | Colon | Human | 10,000 | 2.72 |
| SF-268 | CNS | Human | 15,000 | 4.94 |
| SF-295 | CNS | Human | 10,000 | 12.70 |
| SF-539 | CNS | Human | 15,000 | 0.0075 |
| SNB-19 | CNS | Human | 15,000 | 2.90 |
| SNB-75 | CNS | Human | 20,000 | 7.71 |
| U251 | CNS | Human | 7,500 | 2.19 |
| LOX IMVI | Melanoma | Human | 7,500 | 4.53 |
| M14 | Melanoma | Human | 15,000 | 4.57 |
| SK-MEL-2 | Melanoma | Human | 20,000 | 25.0 |
| SK-MEL-28 | Melanoma | Human | 10,000 | 11.6 |
| SK-MEL-5 | Melanoma | Human | 10,000 | 7.80 |
| UACC-257 | Melanoma | Human | 20,000 | 2.31 |
| UACC-62 | Melanoma | Human | 10,000 | 1.55 |
| IGR-OV1 | Ovarian | Human | 10,000 | 3.11 |
| OVCAR-3 | Ovarian | Human | 10,000 | 13.50 |
| OVCAR-4 | Ovarian | Human | 15,000 | 9.67 |
| OVCAR-5 | Ovarian | Human | 20,000 | 2.81 |
| OVCAR-8 | Ovarian | Human | 10,000 | 2.65 |
| SK-OV-3 | Ovarian | Human | 20,000 | 4.00 |
| 786-0 | Renal | Human | 10,000 | 6.99 |
| A498 | Renal | Human | 25,000 | 22.30 |
| ACHN | Renal | Human | 10,000 | 3.10 |
| CAKI-1 | Renal | Human | 10,000 | 15.20 |
| RXF 393 | Renal | Human | 15,000 | 7.71 |
| SN12C | Renal | Human | 15,000 | 3.85 |
| UO-31 | Renal | Human | 15,000 | 19.70 |
| DU-145 | Prostate | Human | 10,000 | 3.56 |
| MCF7 | Breast | Human | 10,000 | 10.10 |
| NCI/ADR-RES | Breast | Human | 15,000 | 18.30 |
| MDA-MB-231/ATCC | Breast | Human | 20,000 | 2.72 |
| HS 578T | Breast | Human | 20,000 | 2.76 |
| MDA-MB-435 | Breast | Human | 15,000 | 15.30 |
| BT-549 | Breast | Human | 20,000 | 0.11 |
| T-47D | Breast | Human | 20,000 | 0.77 |

The results indicate that the compound of Formula II was effective against most of the human tumor cell lines that have been assayed in the NCI screening panel suggesting a broad anticancer activity against several types of human cancer.

Example 6

In Vitro Antiproliferative Study Against a Panel of Glioma Cell Lines

The anticancer activity of the compound of Formula II was evaluated using a panel of glioma cancer cell lines shown in Table 5, and the 50% inhibition of cell proliferation ($IC_{50}$) was determined.

Culture conditions: The cell lines listed in Table 5 were shown to be free of mycoplasma infection and were maintained on Dulbecco's modified Eagle medium (DMEM) supplemented with 10% heat-inactivated fetal bovine serum and 1% penicillin-streptomycin, under 5% $CO_2$ at 37° C. Cells were passaged once a week. Prior to use the cells were detached from the culture flask by treating with trypsin for five to ten minutes. The cells were counted with a Neubauer glass slide and viability assessed by 0.25% trypan blue exclusion. Only flasks with >95% cell viability, were used in the study.

Cell lines amplification and plating: Cells, 5×10³ cells per well in 100 μL drug-free medium supplemented with 10% serum, were plated in 96-well flat bottom microtiter plates and incubated at 37° C. for 48 hrs before treatment.

Evaluation of inhibitory activity on cell proliferation: Cells (in triplicate wells) were incubated 96 hrs with medium containing different concentrations of the compound of Formula II, starting at 5.0 μg/ml (10 μM). The compound was used in a solution of 1% DMSO in D-MEM or RPMI media (or other equivalent media). The concentrations of the compound of Formula II were as follows: 10 μM (5.0 μg/ml), 1 μM (0.50 μg/ml), 0.5 μM (0.25 μg/ml), 0.1 μM (0.050 μg/ml), 0.5 μM (0.025 μg/ml), 0.01 μM (0.0050 μg/ml), 0.001 μM (0.00050 μg/ml). Negative controls were cells treated with vehicle alone (1% DMSO in culture medium). Positive controls were cells treated with 4 to 6 increasing concentrations of cisplatin (CDDP) (data not shown). The optical density was measured before incubation (time 0) and following 96 hrs of incubation with test compound in order to measure the growth rate of each cell line.

At the end of the cell treatment, cell culture media was replaced with 150 μl of fresh medium containing 10 mM of 4-(2-hydroxyethyl)-1-piperazineethanesulfonic acid buffer, pH 7.4. Then 50 μl of 2.5 mg/ml of 3-(4,5-dimethylthiazo-2-yl)-2,5-diphenyltetrazolium bromide in PBS pH 7.4, were added to each well and the culture plates incubated for 4 hrs at 37° C. The resulting supernatant was removed and formazan crystals were dissolved with 200 μl of DMSO followed by 25 μl of glycine buffer (0.1 M glycine plus 0.1 M NaCl, pH 10.5). The optical density was read in each well using a single wavelength spectrophotometer plate reader at 570 nm. Results were expressed as the concentration of drug, which inhibits 50% of the cell growth ($IC_{50}$). Each of the cell lines was tested in at least 3 independent experiments.

Results shown in Table 5 confirmed the activity of the compound of Formula II against different brain cancer cell lines including gliosarcoma, which is the most malignant form of type IV glioblastoma multiform. Gliosarcomas are a mixture of glial and endothelial cells and are resistant to any chemotherapy.

TABLE 5

| Cell lines | Type | Origin | Source | $IC_{50}$ ($\times 10^{-6}$ M) |
|---|---|---|---|---|
| 9L | Gliosarcoma | Rat | ATCC | 6.82 ± 2.90 |
| GHD | Astrocytoma | Human | ATCC | 6.29 ± 2.98 |
| U 373 | Astrocytoma | Human | ATCC | 3.83 ± 1.37 |
| GL26 | Glioblastoma | Human | ATCC | 8.93 ± 1.10 |
| C6 | Glioblastoma | Rat | ATCC | 4.28 ± 2.82 |
| DN | Oligodendroglioma | Human | ATCC | 3.26 ± 0.93 |
| GHA | Oligodendroglioma | Human | ATCC | 1.78 ± 0.84 |

Example 7

In Vivo Efficacy in a Glioma Model

The aim of this study was to test whether the compound of Formula II administered by i.p. route prevents or delays tumor growth in C6 glioblastoma cell-bearing mice, and to determine an effective dosage regimen.

Animals: A total of 60 six-week-old female mice (Mus musculus nude mice), ranging between 18 to 25 g in weight, were observed for 7 days before treatment. Animal experiments were performed according to ethical guidelines of animal experimentation (Charte du comité d'éthique du CNRS, juillet 2003) and the English guidelines for the welfare of animals in experimental neoplasia (WORKMAN, P., TWENTYMAN, P., BALKWILL, F., et al. (1998). *United Kingdom Coordinating Committee on Cancer Research (UKCCCR) Guidelines for the welfare of animals in experimental neoplasia* (Second Edition, July 1997; British Journal of Cancer 77:1–10). Any dead or apparently sick mice were promptly removed and replaced with healthy mice. Sick mice were euthanized upon removal from the cage. Animals were maintained in rooms under controlled conditions of temperature (23±2° C.), humidity (45±5%), photoperiodicity (12 hrs light/12 hrs dark) and air exchange. Animals were housed in polycarbonate cages (5/single cage) that were equipped to provide food and water. Animal bedding consisted of sterile wood shavings that were replaced every other day. Food was provided ad libitum, being placed in the metal lid on the top of the cage. Autoclaved tap water was provided ad libitum. Water bottles were equipped with rubber stoppers and sipper tubes. Water bottles were cleaned, sterilized and replaced once a week. Two different numbers engraved on two earrings identified the animals. Each cage was labelled with a specific code.

Tumor Cell Line: The C6 cell line was cloned from a rat glial tumor induced by N-nitrosomethyurea (NMU) by Premont et al. (Premont J, Benda P, Jard S., *[3H] norepinephrine binding by rat glial cells in culture. Lack of correlation between binding and adenylate cyclase activation.* Biochim Biophys Acta. 1975 Feb. 13;381(2):368–76.) after series of alternate culture and animal passages.

Cells were grown as adherent monolayers at 37° C. in a humidified atmosphere (5% $CO_2$, 95% air). The culture medium was DMEM supplemented with 2 mM L-glutamine and 10% fetal bovine serum. For experimental use, tumor cells were detached from the culture flask by a 10 min treatment with trypsin-versen. The cells were counted in a hemocytometer and their viability assessed by 0.25% trypan blue exclusion.

Preparation of the Test Article: For the test article, the following procedure was followed for reconstitution (performed immediately preceding injection). The vehicle consisted of a mixture of benzyl alcohol (1.5%), ethanol (8.5%), propylene glycol (PG) (27%), Polyethylene glycol (PEG) 400 (27%), dimethylacetamide (6%) and water (30%). The vehicle solution was first vortexed in order to obtain a homogeneous liquid. 0.6 mL of the vortexed vehicle solution was added to each vial containing the test article (the compound of Formula II). Vials were mixed thoroughly by vortexing for 1 minute and inverted and shaken vigorously. Vials were mixed again prior to injection into each animal.

Animal Inoculation with tumor cells: Experiment started at day 0 ($D_0$). On $D_0$, mice received a superficial intramuscular injection of C6 tumor cells ($5 \times 10^5$ cells) in 0.1 mL of DMEM complete medium into the upper right posterior leg.

Treatment Regimen and Results

Figure 9:
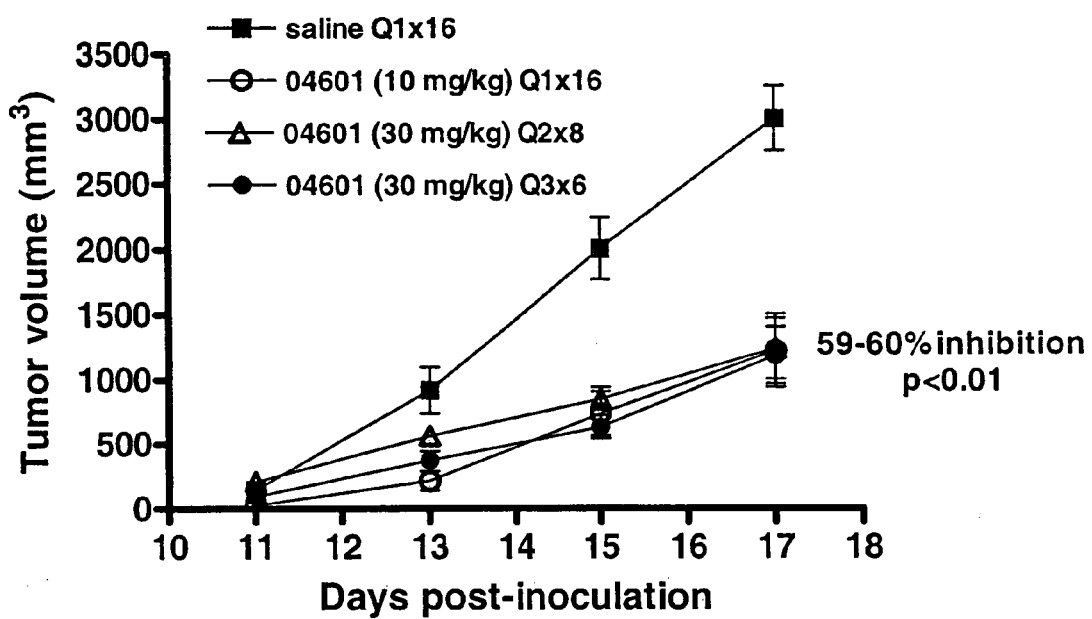
FIG. 9 shows inhibition of tumor growth resulting from administration of 10 to 30 mg/kg of the compound of Formula II to glioblastoma-bearing mice beginning one day after tumor cell inoculation.

In a first series of experiments, treatment started 24 hrs following inoculation of C6 cells. On the day of the treatment, each mouse was slowly injected with 100 μL of test or control articles by i.p. route. For all groups, treatment was performed until the tumor volume of the saline-treated mice (group 1) reached approximately 3 cm³ (around day 16). Mice of group 1 were treated daily with a saline isosmotic solution for 16 days. Mice of group 2 were treated daily with the vehicle solution for 16 days. Mice of group 3 were treated daily with 10 mg/kg of the compound of Formula II for 16 days. Mice of group 3 were treated every two days with 30 mg/kg of the compound of Formula II and received 8 treatments. Mice of group 5 were treated every three days with 30 mg/kg of the compound of Formula II and received 6 treatments. Measurement of tumor volume started as soon as tumors became palpable (>100 mm³; around day 11 post-inoculation) and was evaluated every second day until the end of the treatment using callipers. As shown in Table 6 and FIG. 9, the mean value of the tumor volume of all the compound of Formula II treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 6 indicates a statistically significant value, while "ns" signifies not significant.

TABLE 6

| Treatment | Treatment regimen | Tumor volume (mm³) (mean ± SEM) | % Inhibition | P value |
|---|---|---|---|---|
| Saline | Q1 × 16 | 3,004.1 ± 249.64 | — | — |
| Vehicle solution | Q1 × 16 | 2,162.0 ± 350.0 | 28.0% | >0.05 ns |
| Formula II (10 mg/kg) | Q1 × 16 | 1,220.4 ± 283.46 | 59.4% | <0.01* |
| Formula II (30 mg/kg) | Q2 × 8 | 1,236.9 ± 233.99 | 58.8% | <0.01* |
| Formula II (30 mg/kg) | Q3 × 6 | 1,184.1 ± 221.45 | 60.6% | <0.01* |

Figure 10:
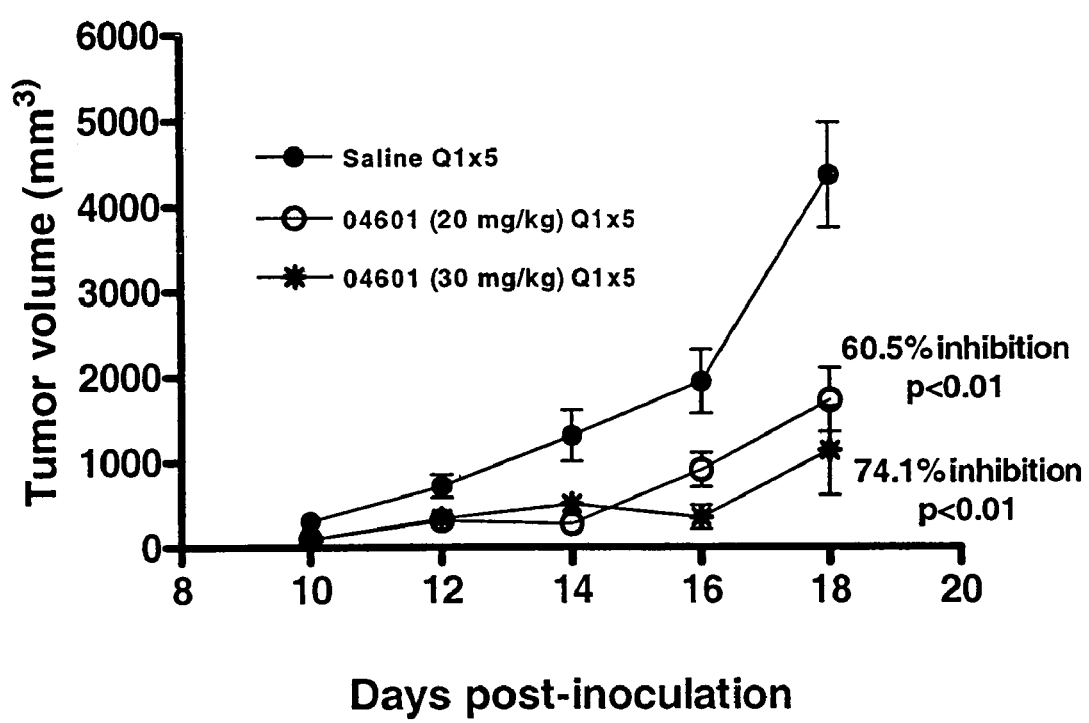
FIG. 10 shows inhibition of tumor growth resulting from administration of 20–30 mg/kg of the compound of Formula II to glioblastoma-bearing mice beginning ten days after tumor cell inoculation.

In a second series of experiments, treatment started at day 10 following inoculation of C6 cells when tumors became palpable (around 100 to 200 mm³). Treatment was repeated daily for 5 consecutive days. On the day of the treatment, each mouse was slowly injected with 100 μL of the compound of Formula II by i.p. route. Mice of group 1 were treated daily with saline isosmotic solution. Mice of group 2 were treated daily with the vehicle solution. Mice of group 3 were treated daily with 20 mg/kg of the compound of Formula II. Mice of group 4 were treated daily with 30 mg/kg of the compound of Formula II. Mice were treated until the tumor volume of the saline-treated control mice (group 1) reached around 4 cm³. Tumor volume was measured every second day until the end of the treatment using callipers. As shown in Table 7 and FIG. 10, the mean value of the tumor volume of all the compound of Formula II treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 7 indicates a statistically significant value, while "ns" signifies not statistically significant.

Figure 11:
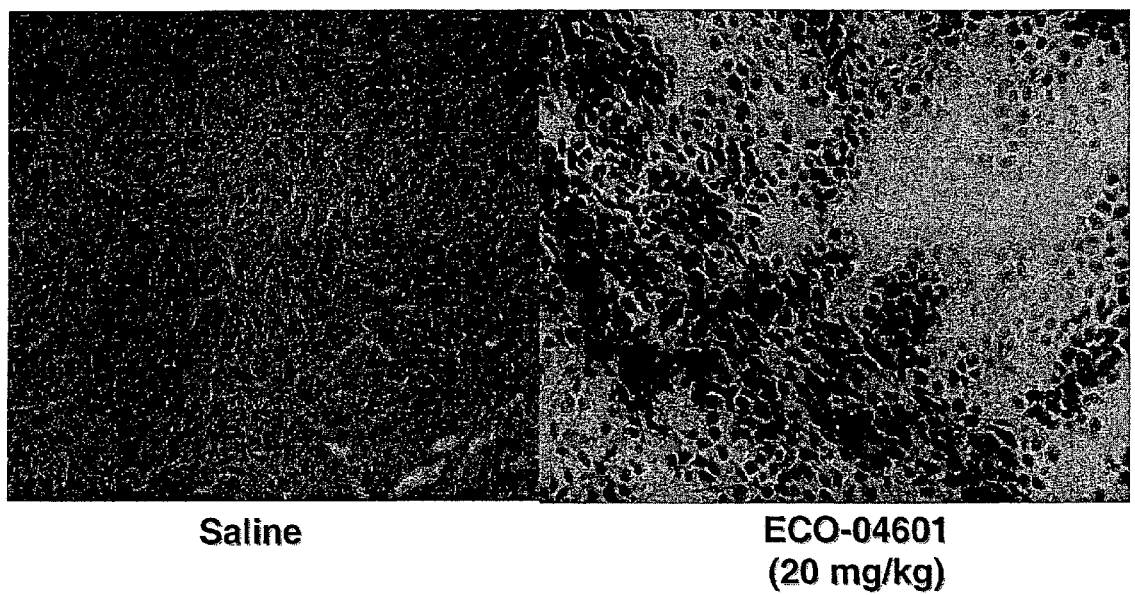
FIG. 11 shows micrographs of tumor sections from mice bearing glioblastoma tumors and treated with saline or the compound of Formula II. The cell density of tumor treated with the compound of Formula II appears decreased and nuclei from tumor cells treated with the compound of Formula II are larger and pynotic suggesting a cytotoxic effect.

Histological analysis of tumor sections showed pronounced morphological changes between tumors treated with the compound of Formula II and control groups. In tumors treated with treated tumors (20–30 mg/kg), cell density was decreased and the nuclei of remaining tumor cells appeared larger and pycnotic while no such changes were observed for vehicle-treated mice (FIG. 11).

TABLE 7

| Treatment | Treatment regimen | Tumor volume (mm³) (mean ± SEM) | % Inhibition | P value |
|---|---|---|---|---|
| Saline | Q1 × 5 | 4,363.1 ± 614.31 | — | — |
| Vehicle solution | Q1 × 5 | 3,205.0 ± 632.37 | 26.5% | >0.05 ns |
| Formula II (20 mg/kg) | Q1 × 5 | 1,721.5 ± 374.79 | 60.5% | <0.01* |
| Formula II (30 mg/kg) | Q1 × 5 | 1,131.6 ± 525.21 | 74.1% | <0.01* |

Example 8

Antitumor Efficacy of the Compound of Formula II Against Orthotopic C6 Glioma Tumor Xenograft The antitumor activity of the compound of formula II was further tested in a orthotopic C6 glioma tumor xenograft model in mice. CD1 female nude mice (6 weeks of age) were grafted intra-cerebally with $5 \times 10^4$ (volume of 10 microliters) rat C6 glioma cells (day 0). Treatment was initiated 24 h after tumor cell implantation. The compound of Formula II was administered intraperitoneally (i.p.) at a concentration of 30 mg/kg (volume of 10 mL/Kg) on days 1, 2 and 3 followed by i.p. injections of 10 mg/kg on days 4 and 5 and 9 to 38. Vehicle (30% PEG; 30% PG; 40% H2O) was injected in a volume of 10 mL/Kg using the same route and schedule.

Figure 17:
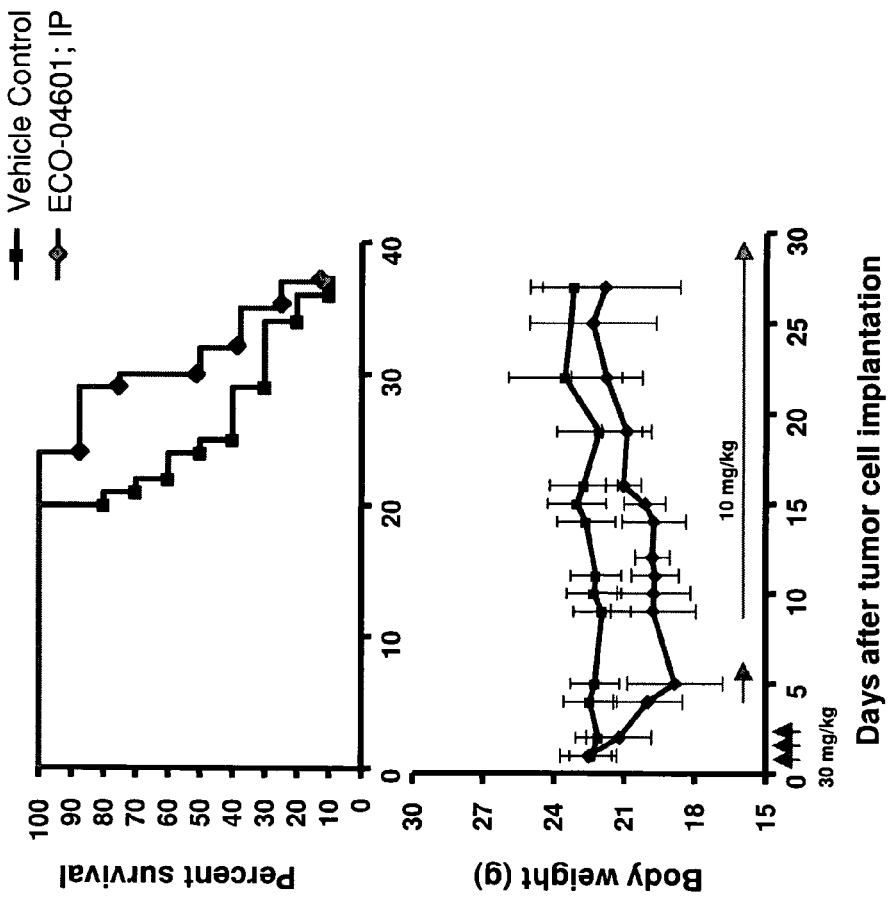
FIG. 17 shows the survival of mice xenografted with orthotopic C6 glioma tumor, treated daily with vehicle (squares) or the compound of Formula II (circles). Daily treatment with the compound of Formula II led to an increase survival of 7 days resulting in a 29% increase in life span.

Body weight of animals was monitered every other day and the effect of the compound of Formula II on growth of intracerebral glioma tumors was evaluated by mouse survival and percentage increase in life span (% ILS, expressed as mean survival time of treated animals minus that of control animals over the mean survival time of the control group). By criteria established by the National Cancer Institute, increases in life span exceeding 25% indicate that the drug has significant antitumor activity (Plowman et al. (1997) Human tumor xenografts models in NCI drug development. In: Theicher B A (ed) Anticancer drug development guide: prescreening, clinical trials and approval. Human press, Totowa, pp 101–125). Statistical analysis of mouse survival was performed by Kaplan-Mayer analysis. Daily treatment with the compound of Formula II led to an increase survival of 7 days resulting in a 29% increase in life span (see FIG. 17).

Example 9

Pharmacokinetics

Preparation of the Test Article: The compound of Formula II was dissolved in 300 microliters of propylene glycol (PG). A volume of 300 microliters of poly(ethylene glycol) 400 (PEG 400) was added to PG solution. Then, a volume of 400 microliters of water was further added to the mixture, resulting in drug concentration of 20 to 22.5 mg/mL. The volume ratio of PEG 400/PG/water was respectively 30:30:40. The aqueous PEG/PG formulation was injected in animals.

Animal Administration: CD1 female mice (6 weeks of age) received a single oral (225 mg/kg; 10 mL/kg), intraperitoneal (30 mg/kg; 10 mL/kg), subcutaneous (225 mg/kg; 10 mL/kg), and intraveneous (100 mg/kg; 5 mL/kg) dose of the compound of Formula II in the PEG-PG formulation described above. Two mice per group were sacrificed at 3 min, 10 min, 30 min, 1 h, 2 h, 4 h, 8 h, 24 h and 48 h. Blood was collected into EDTA containing tubes by cardiac puncture and brains were rapidly collected and immediately frozen on dry ice. Samples were analysed by LC/MS/MS. Standard curve ranged from 25 to 2000 ng/mL with limit of quantitation ("LOQ")≦15 ng/mL.

Pharmacokinetics

Plasma and brain concentration values of the compound of Formula II falling below the limit of quantitation (LOQ) were set to zero. Mean concentration values and standard deviation (SD) were calculated at each timepoints of the pharmacokinetic study (n=2 animals/timepoint). The following pharmacokinetic parameters were calculated: area under the plasma concentration versus time curve from time zero to the last measurable concentration time point (AUC0-t), area under the plasma concentration versus time curve extrapolated to infinity (AUCinf), maximum observed plasma concentration (Cmax), time of maximum plasma concentration (Tmax), apparent first-order terminal elimination rate constant (kel), apparent first-order terminal elimination half-life will be calculated as 0.693/kel (T½). The systemic clearance (CL) of the compound of Formula II after intravenous administration was calculated using Dose/AUCinf. The apparent clearance (CL/F) after intraperitoneal, subcutaneous and oral administrations were calculated using Dose/AUCinf. Bioavailability following subcutaneous administration of the compound of Formula II was calculated as (AUCinfSC/DoseSC)/(AUCinfIV/DOSEIN). Bioavailability following oral administration of the compound of Formula II was calculated as (AUCinfPO/DosePO)/(AUCinfIV/DOSEIN). Pharmacokinetic parameters were calculated using Kinetica™ 4.1.1 (InnaPhase Corporation, Philadelphia, Pa.).

Results

Compound of Formula II in Plasma

Figure 15:
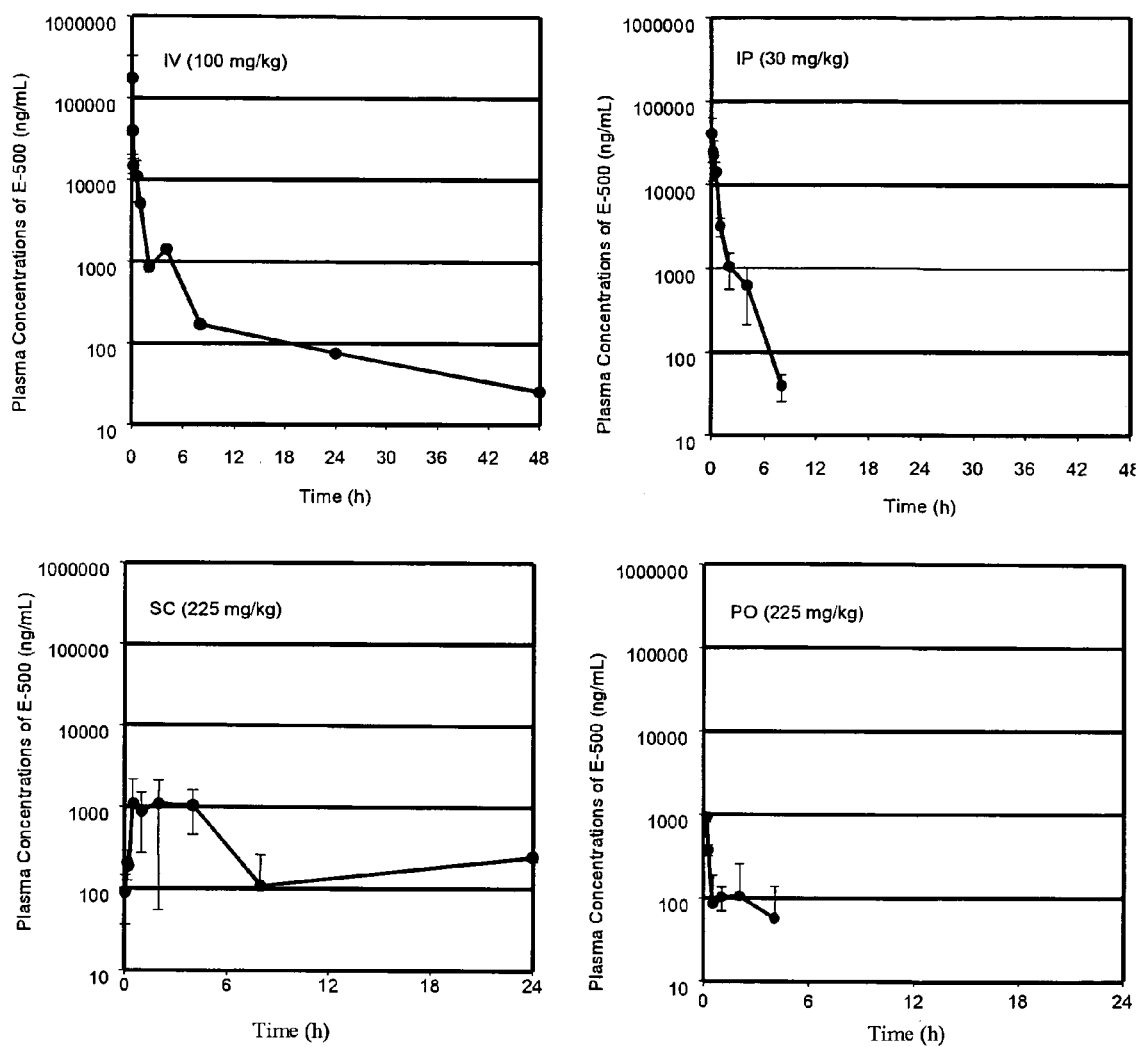
FIG. 15 shows the mean (±SD) plasma concentrations of the compound of Formula II following intravenous (I.V. 100 mg/kg), intraperitoneal (I.P., 30 mg/kg), subcutaneous (SC, 225 mg/kg) and oral (PO, 225 mg/kg) administrations.

Mean (±SD) plasma concentrations of the compound of Formula II following intravenous (I.V. 100 mg/kg), intraperitoneal (I.P., 30 mg/kg), subcutaneous (SC, 225 mg/kg) and oral (PO, 225 mg/kg) administrations are presented in FIG. 15.

Mean plasma concentrations of the compound of Formula II following I.V. administration of a 100 mg/kg dose declined in a biexponential manner and remained above the LOQ for 48 hours. On the other hand, the pharmacokinetics of the compound of Formula II following intraperitoneal administration of a 30 mg/kg dose was characterized over a shorter timeframe since all concentrations values fell below the LOQ after 8 hours. Mean plasma concentrations of the compound of Formula II following SC administration reached plateau concentrations around 1000 ng/mL during approximately 4 hours after drug administration. Oral administration of the compound of Formula II resulted in very low plasma concentrations. All plasma concentrations of the compound of Formula II fell below the LOQ 4 hours after oral administration of a 225 mg/kg dose. Pharmacokinetics parameters of the compound of Formula II in plasma are presented below.

|  | IV | IP | SC | PO |
|---|---|---|---|---|
| Dose (mg/kg) | 100 | 30 | 225 | 225 |
| Cmax (ng/mL) | 173088 | 40679 | 1078 | 930 |
| Tmax (h) | 0.025 | 0.05 | 2.00 | 0.167 |
| AUC0-t (ng · h/mL) | 27985 | 20931 | 8837 | 505 |
| AUCinf (ng · h/mL) | 28520 | 21000 | 15416 | 781 |
| T½ (h) | 14.6 | 1.22 | 18.8 | 3.31 |
| CL (L/h/kg) | 3.51 | N/A | N/A | N/A |
| CL/F (L/h/kg) | N/A | 1.43 | 14.6 | 288.1 |
| F % | N/A | N/A | 24.0% | 1.22% |

IV: intravenous administration,
IP: intraperitoneal administration,
SC: subcutaneous administration,
PO: oral administration.

The pharmacokinetics of the compound of Formula II in plasma following IV administration was well characterized over 48 hours. The systemic clearance of Formula II (CL=3.51 L/h/kg) was very close to the liver blood flow in mice (ie., 13.8 mL/min for a 0.250 kg mice=3.3 L/h/kg). The bioavailability of the compound of Formula II following subcutaneous and oral administrations were 24.0% and 1.22%, respectively.

Compound of Formula II in Brain Tissues

Figure 16:
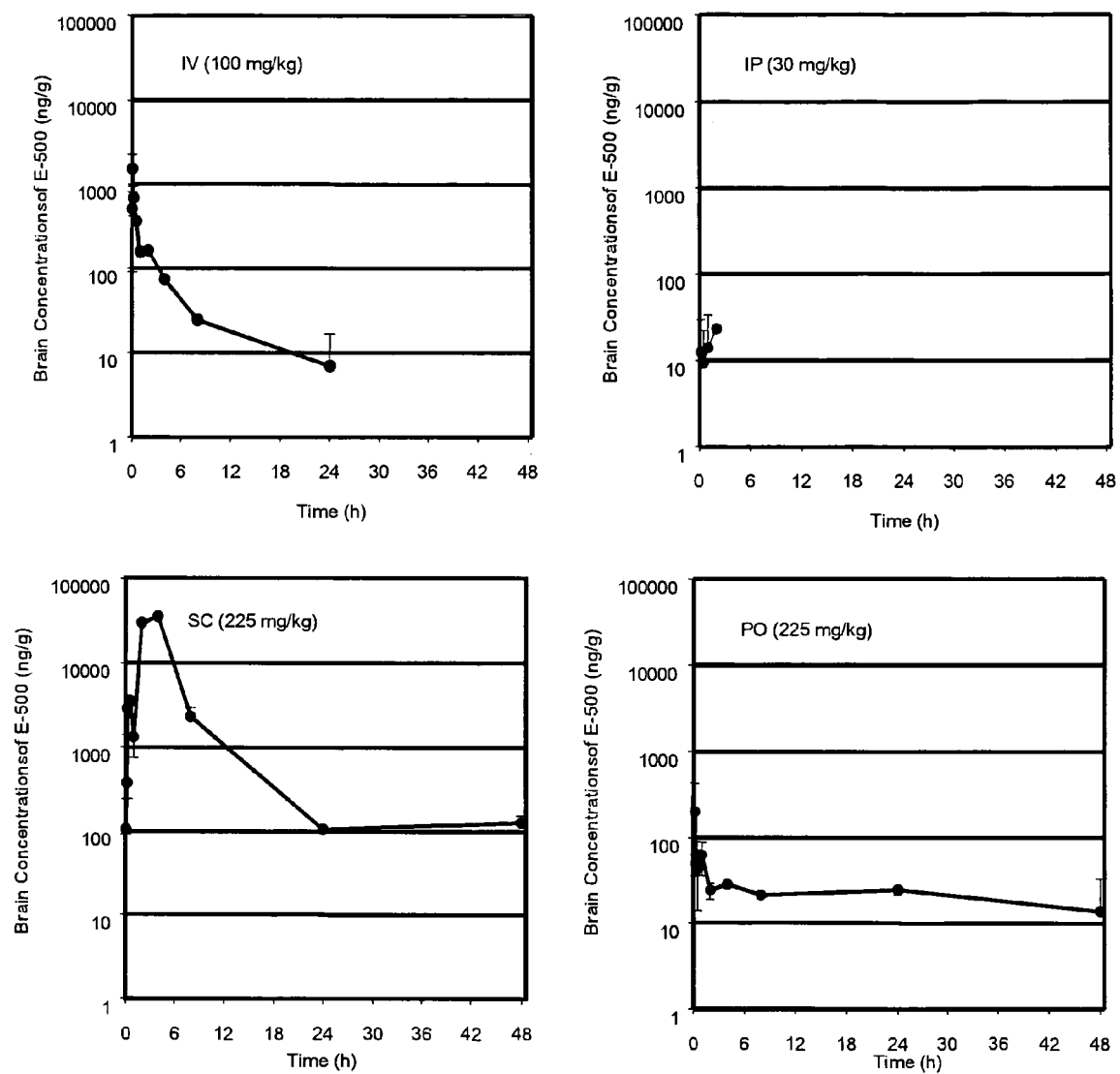
FIG. 16 shows the mean (±SD) brain concentrations of the compound of Formula II following intravenous (IV, 100 mg/kg), intraperitoneal (IP, 30 mg/kg), subcutaneous (SC, 225 mg/kg) and oral (PO, 225 mg/kg) administrations.

Mean (±SD) brain concentrations of the compound of Formula II following intravenous (IV, 100 mg/kg), intraperitoneal (IP, 30 mg/kg), subcutaneous (SC, 225 mg/kg) and oral (PO, 225 mg/kg) administrations are presented in FIG. 16.

The pharmacokinetic profile of the compound of Formula II in brain tissues following IV administration of a 100 mg/kg dose was well characterized over 24 hours. The pharmacokinetic profile of the compound of Formula II in brain was similar to that observed in plasma (ie,. biexponential elimination), suggesting that the brain and plasma concentrations of the compound of Formula II are in rapid equilibrium. On the other hand, the pharmacokinetics of the compound of Formula II following intraperitoneal administration of a 30 mg/kg dose was characterized over a shorter timeframe since all concentrations values fell below the LOQ after 8 hours.

Mean concentrations of the compound of Formula II in brain tissues following SC administration were very high (range: 300–35500 ng/mL). These high concentrations values could not be explained pharmacokinetically since they were markedly lower than those observed in plasma (range: 70–1078 ng/mL). These unexpected high concentration values in brain tissues may be associated to severe edema around the site of injection (arm and shoulder) and underneath the skin of the cranium. It is possible that the area of edema contaminated the brain concentrations when the animals were sacrificed.

Oral administration of the compound of Formula II resulted in very low plasma concentrations. All plasma concentrations of the compound of Formula II fell below the LOQ 4 hours after oral administration of a 225 mg/kg dose. Pharmacokinetics parameters of the compound of Formula II in brain tissues following the IV, IP, SC and PO routes of administration are presented below.

|  | IV | IP | SC | PO |
|---|---|---|---|---|
| Dose (mg/kg) | 100 | 30 | 225 | 225 |
| Cmax (ng/g) | 1533 | 23.5 | NC | 199 |
| Tmax (h) | 0.05 | 2 | NC | 0.167 |
| AUC0–t (ng · h/g) | 1316 | 29.0 | NC | 1076 |
| AUCinf (ng · h/g) | 1381 | NC | V | 1648 |
| T½ (h) | 6.46 | NC | NC | 29.0 |

IV: intravenous administration,
IP: intraperitoneal administration,
SC: subcutaneous administration,
PO: oral administration.

Maximum brain concentrations of the compound of Formula II following intravenous administration was markedly higher than that observed following oral administration (1533 vs 199 ng/g). On the other hand, the exposure of the compound of Formula II in brain tissues following intravenous and oral administrations were similar (ie, 1381 and 1648 ng.g/h) since the pharmacokinetics of the compound of Formula II following oral administration was associated to a longer elimination half-life (ie., 29 hours). Considering the difference in doses between the two routes of administration, the exposure of the compound of Formula II in brain tissues following oral administration (1648 divided by 2.25) would be approximately two-fold lower than that observed after intravenous administration (1381 ng.h/g).

Example 10

Generation of Variants of the Compound of Formula II According to the Invention

Variants of the compound of Formula II molecule, for example those identified herein as Formulae III–LIX, can be generated by standard organic chemistry approaches. General principles of organic chemistry required for making and manipulating the compounds described herein, including functional moieties, reactivity and common protocols are described, for example, in "Advanced Organic Chemistry," 3$^{rd}$ Edition by Jerry March (1985) which is incorporated herein by reference in its entirety. In addition, it will be appreciated by one of ordinary skill in the art that the synthetic methods described herein may use a variety of protecting groups, whether or not they are explicitly described. A "protecting group" as used herein means a moiety used to block one or more functional moieties such as reactive groups including oxygen, sulfur or nitrogen, so that a reaction can be carried out selectively at another reactive site in a polyfunctional compound. General principles for the use of protecting groups, their applicability to specific functional groups and their uses are described for example in T. H. Greene and P. G. M. Wuts, Protective Groups in Organic Synthesis, 3$^{rd}$ Edition, John Wiley & Sons, New York (1999).

Scheme 1: Epoxide Variants

The epoxide compounds of the present invention (e.g., compounds according to exemplary Formulae VII–XIV) are made from the compound of Formula II by treatment with any of a number of epoxidizing reagents such as perbenzoic acid, monoperphthalic acid or more preferably by m-chloroperbenzoic acid in an inert solvent such as tetrahydrofuran (THF) dichloromethane or 1,2-dichloroethane. It will be appreciated by one of ordinary skill in the art that slightly greater than one molecule equivalent of epoxidizing agent will result in the maximal yield of mono-epoxides, and that the reagent, solvent, concentration and temperature of the reaction will dictate the ratio of specific mono-epoxides formed. It will also be appreciated that the mono-epoxides will be enantiomeric mixtures, and that the di-epoxides and the tri-epoxide can be prepared as diastereomers and that the conditions of the reaction will determine the ratios of the products. One skilled in the art will appreciate that under most conditions of reactions the product will be a mixture of all possible epoxides and that these may be separated by standard methods of chromatography. Exemplary approaches to the generation of mono-, di-, and tri-epoxides are provided below.

A) Mono-epoxides of the Formulae VII, VIII, and IX by epoxidation of the compound of Formula II:

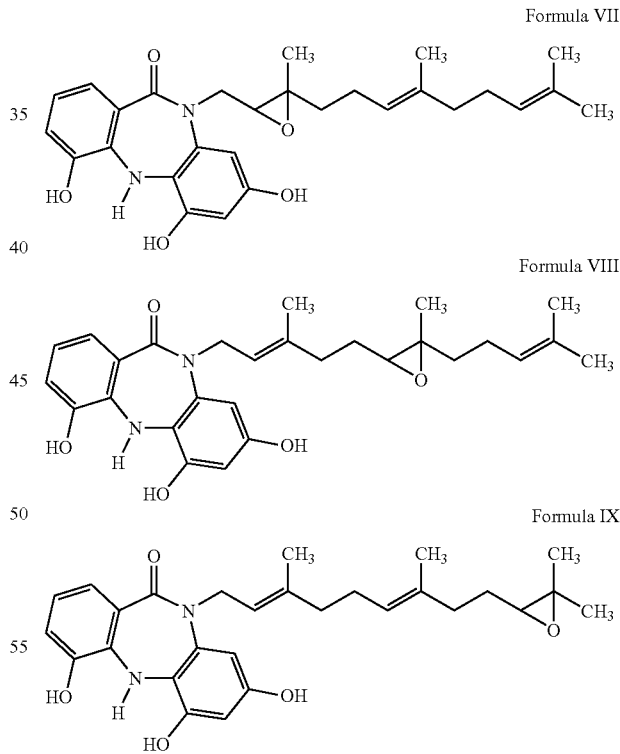

To a solution of the compound of Formula II dissolved in tetrahydrofuran (THF) is added 1.1 equivalents of meta-chloroperbenzoic acid. The reaction is cooled in an ice bath and stirred at 0° C. for 1–2 hours. The reaction mixture is then evaporated to dryness, re-dissolved in methanol and subjected to liquid chromatography on a column of Sephadex LH-20 to isolate a mixture of predominantly the compounds of Formulae VII, VIII and IX, contaminated with some unchanged starting material and some di- and tri-epoxides. The compounds of Formulae VII, VIII and XIX are separated and purified by HPLC using the system described in Example 2 for the purification of the compound of Formulae II. In a typical experiment yields of 15% to 25% are obtained for each of the compounds of Formulae VII, VIII and IX.

B) Synthesis of Compounds of Formulae X, XI, and XII by di-epoxidation of Compound of Formula II:

Formula X

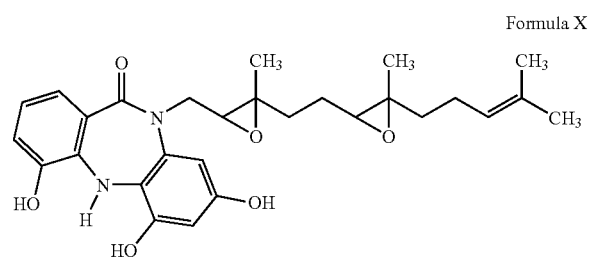

Formula XI

Formula XII

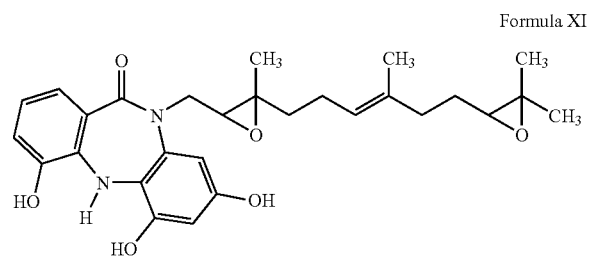

To a solution of the compound of Formula II dissolved in tetrahydrofuran (THF) is added 2.3 equivalents of meta-chloroperbenzoic acid. The reaction is cooled in an ice bath and stirred at 0° C. for 1–2 hours. The reaction mixture is then evaporated to dryness, re-dissolved in methanol and subjected to liquid chromatography on a column of Sephadex LH-20 to isolate a mixture of predominantly the compounds of Formulae X, XI and XII, contaminated with traces of unchanged starting material and some mono- and tri-epoxides. The Compounds of Formulae X, XI and XII are separated and purified by HPLC using the system described in Example 2 for the purification of the compound of Formulae II. In a typical experiment, yields of 15% to 20% are obtained for each of the compounds of Formulae X, XI and XII.

C) Synthesis of Compound of Formula XIII by tri-epoxidation of Compound of Formula II:

Formula XIII

To a solution of the compound of Formula II, dissolved in tetrahydrofuran (THF), is added 3.5 equivalents of meta-chloroperbenzoic acid. The reaction is cooled in an ice bath and stirred at 0° C. for 1–2 hours. The reaction mixture is then evaporated to dryness, re-dissolved in methanol and subjected to liquid chromatography on a column of Sephadex LH-20 to isolate the compound of Formula XII as a mixture of diasteriomers in a yield of 80+%.

Scheme 2: Synthesis of Compound of
Formula III by N-acetylation of Compound of Formula II Formula III To a solution of Compound of Formula II dissolved in tetrahydrofuran (THF) is added 1.2 equivalents of acetic anhydride and a few drops of triethylamine. The reaction mixture allowed to stand at room temperature for 1–2 hours and then evaporated to dryness under reduced pressure to obtain the Compound of Formula IIII in an essentially pure form in an almost quantitative yield Scheme 3: Syntheses of Compounds of
Formulae IV and V by N-alkylation of Compound of Formula II

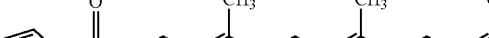

Formula IV R = benzyl
Formula V R = ethyl

To a solution of Compound of Formula II dissolved in terachloroethylene is added 1.2 equivalents of the appropriate alkyl bromide (benzyl bromide for the compound of formula IV or ethyl bromide for the Compound of Formula V). The reaction mixture the reaction mixture is heated under reflux for 1–2 hours and then evaporated to dryness under reduced pressure to obtain the Compound of Formula IV or the Compound of Formula V respectively, in an essentially pure form in an almost quantitative yield.

Scheme 4: Syntheses of Compounds of Formulae XL, XLI and XLII by catalytic reduction of Compound of Formula II

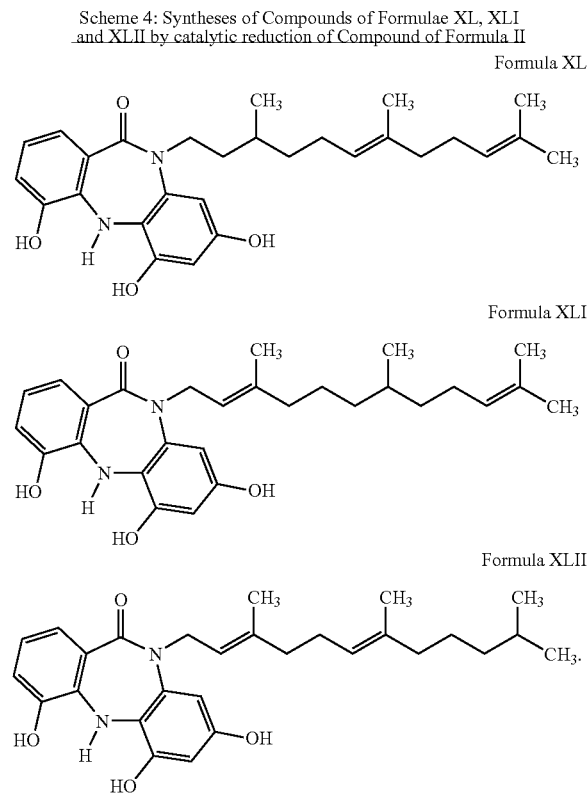

A solution of the Compound of Formula II (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where one millimole of hydrogen has been consumed, shaking is stopped, the vessel is rapidly evacuated and the atmosphere is replaced with nitrogen. The catalyst is removed by filtration and the filtrate is concentrated to obtain a crude mixture of the Compounds of Formulae XL, XLI and XLII contaminated by unreacted starting material and minor amounts of over reduced products. The desired products may be separated and purified by HPLC or HSCC chromatography using the systems as described in Example 2 above, to obtain approximately 100 mg of each of the Compounds of Formulae XL, XLI and XLII.

Scheme 5: Syntheses of Compounds of Formulae XLIII, XLIV and XLV by catalytic reduction of Compound of Formula II

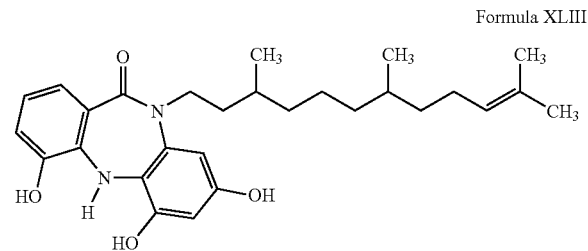

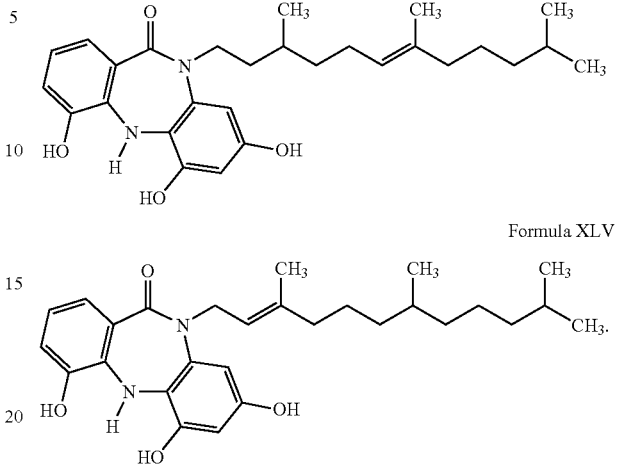

A solution of the Compound of Formula II (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where two millimoles of hydrogen has been consumed, shaking is stopped, the vessel is rapidly evacuated and the atmosphere is replaced with nitrogen. The catalyst is removed by filtration and the filtrate is concentrated to obtain a crude mixture of the Compounds of Formulae XLIII, XLIV and XLV contaminated by trace amounts unreacted starting material and minor amounts of under and over reduced products. The desired products may be separated and purified by HPLC or HSCC chromatography using the systems as described in Example 2 above, to obtain approximately 100 mg of each of the Compounds of Formulae XLIII, XLIV and XLV.

Scheme 6: Syntheses of Compound of Formulae XLVI by catalytic reduction of Compound of Formula II

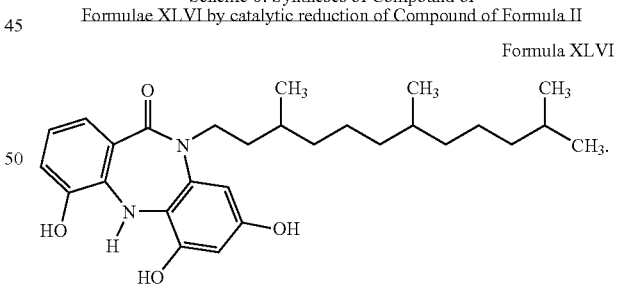

A solution of the Compound of Formula II (462 mg) in ethanol (200 ml) with palladium on charcoal (25 mg of 5%) is shaken in an hydrogenation apparatus in an atmosphere of hydrogen. The uptake of hydrogen by the reaction is measured carefully and at the point where three millimoles of hydrogen has been consumed, shaking is stopped, the vessel is rapidly evacuated and the atmosphere is replaced with nitrogen. The catalyst is removed by filtration and the filtrate is concentrated to obtain an essentially pure sample of the Compound of Formula XLVI

Scheme 7: Syntheses of Compound of Formula VI by peracetylation of Compound of Formula II

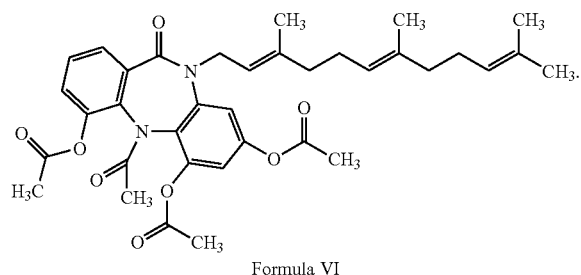

Formula VI

A solution of the Compound of Formula II (100 mg) in acetic anhydride (5 ml) is treated with pyridine (250 ul). The reaction mixture is allowed to stand overnight at room temperature and is then diluted with toluene (100 ml). The toluene solution is washed well with aqueous 5% sodium bicarbonate solutions, then with water and is finally concentrated under reduced pressure to give an essentially pure sample of the Compound of Formula VI in almost quantitative yield.

Scheme 8: Syntheses of Compound of Formula LI by opening the epoxide of Compound of Formula VII

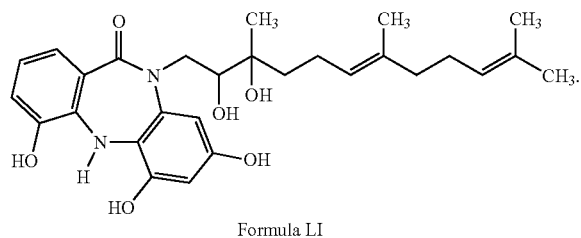

Formula LI

A solution of the Compound of Formula VII (100 mg) in tetrahydrofuran (50 ml) is treated with 1N aqueous hydrochloric acid (5 ml). The reaction mixture is stirred overnight at room temperature and is then diluted with toluene (100 ml) and water (200 ml). The toluene layer is separated and the aqueous layer is extracted with a further 100 ml of toluene. The combined toluene layers are washed once more with water (50 ml) and the separated and dried under vacuum to give the vicinal glycol Compound of Formula LI.

Scheme 9: Syntheses of Compounds of Formulae XLVII, XLIX and LI by ozonolysis of Compound of Formula II

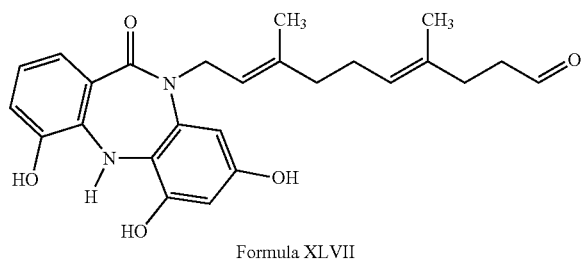

Formula XLVII

-continued

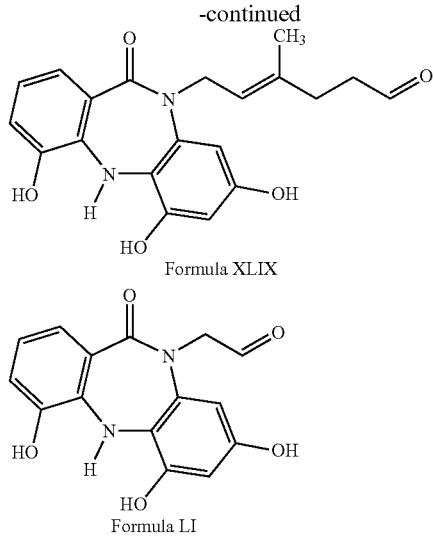

Formula XLIX

Formula LI

A solution of the Compound of Formula II (462 mg) in dry ethyl acetate (200 ml) in an ozonolysis apparatus is cooled to below −20° C. A stream of ozone-containing oxygen is passed into the solution from an ozone generator, which has been precalibrated such that the rate of ozone generation is known. To obtain predominantly the compound of Formula XLVII the passage of ozone is halted after 0.9 millimole have been generated. To obtain predominantly the compound of Formula XLIX the ozone passage is halted after 2 millimoles have been generated and to obtain the compound of Formula LI as the predominant product 3.3 millimoles of ozone are generated.

At the completion of the ozonolysis, the reaction mixture is transferred to an hydrogenation apparatus, 5% palladium on calcium carbonate catalyst (0.2 g) is added to the reaction mixture which is maintained at less than −20° C. and is hydrogenated. When hydrogen uptake is complete the hydrogen atmosphere is replaced with nitrogen and the reaction mixture is allowed to come to room temperature, filtered to remove catalyst and the filtrate is concentrated. The crude product may be purified by chromatography using either HPLC or HSCC with the systems as described in Example 2 to give, dependent on the amount of ozone used, Compounds of Formulae XLVII, XLIX and LI.

Scheme 10: Synthesis of Compound of Formulae XLVIII by reduction of the aldehyde of Compound of Formula XLVII

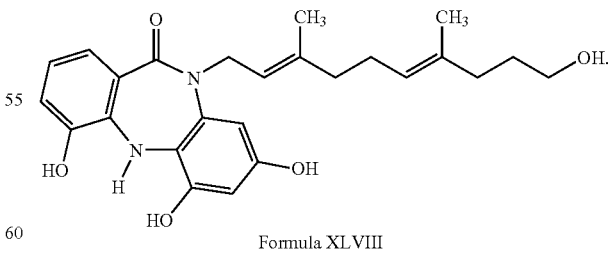

Formula XLVIII

A solution of the Compound of Formula XLVIII (50 mg) in isopropanol (5 ml) is cooled in an ice-salt bath and sodium borohydride (10 mg) is added and the mixture is stirred for 20 minutes. It is then diluted with water (20 ml) and extracted twice with toluene (10 ml portions) at ambient temperature. The combined toluene extracts are filtered and the filtrate is concentrated to give the Compound of Formula XLVII.

Scheme 11: Syntheses of Compounds of Formulae XIV and XV by expoxidation of the Compound of Formula XLII

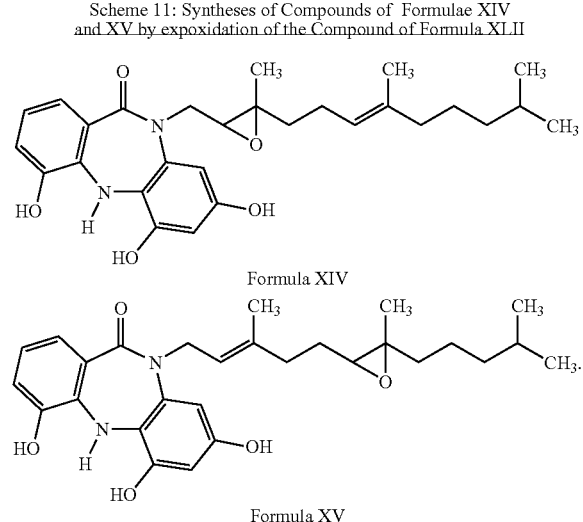

Formula XIV

Formula XV

To a solution of Compound of Formula XLII dissolved in tetrahydrofuran (THF) is added 1.1 equivalents of meta-chloroperbenzoic acid. The reaction is cooled in an ice bath and stirred at 0° C. for 1–2 hours. The reaction mixture is then evaporated to dryness, re-dissolved in methanol and subjected to liquid chromatography on a column of Sephadex LH-20 to isolate a mixture of predominantly the Compounds of Formulae XIV, and XV, contaminated with some unchanged starting material and some diepoxide. The Compounds of Formulae XIV and XV are separated and purified by HPLC or HSCC using one of the systems described in Example 2 for the purification of the Compound of Formulae II. In a typical experiment yields of 35% to 40% are obtained for each of the Compounds of Formulae XIV and XV.

Scheme 12: Synthesis of Compound of Formulae XIX by expoxidation of the Compound of Formula XL

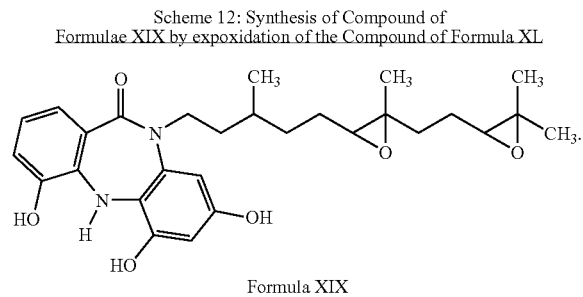

Formula XIX

To a solution of Compound of Formula XL dissolved in tetrahydrofuran (THF) is added 2.2 equivalents of meta-chloroperbenzoic acid. The reaction is cooled in an ice bath and stirred at 0° C. for 1–2 hours. The reaction mixture is then evaporated to dryness, re-dissolved in methanol and subjected to liquid chromatography on a column of Sephadex LH-20 to isolate essentially pure Compound of Formulae XIX in good yield.

Scheme 13: Syntheses of Compounds of Formulae XXVI, XXVII and XXVIII by esterification of the Compound of Formula II

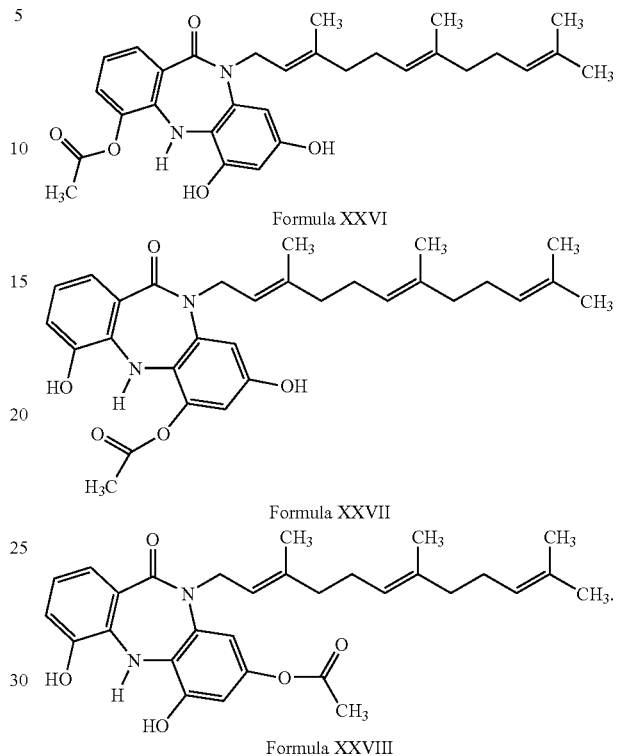

Formula XXVI

Formula XXVII

Formula XXVIII

To a solution of Compound of Formula II dissolved in toluene (9 parts) tetrahydrofuran (1 part), cooled in an ice-bath is added 1.1 equivalents of acetic anhydride and two drops of boron trifluoride etherate. The reaction is maintained cool in an ice bath and stirred at 0° C. for 1–2 hours. The reaction mixture is then poured into aqueous 5% sodium bicarbonate solution shaken and the toluene layer is removed. The aqueous layer is re-extracted with toluene and the combined toluene layers are concentrated to a mixture of predominantly the Compounds of Formulae XXVI, XXVII and XXVIII, contaminated with some unchanged starting material and some diacetates. The Compounds of Formulae XXVI, XXVII and XXVIII are separated and purified by HPLC or HSCC using one of the systems described in Example 2 for the purification of the Compound of Formulae II. In a typical experiment yields of 25% to 30% are obtained for each of the Compounds of Formulae XXVI, XXVII and XXVIII.

Scheme 14: Syntheses of Compounds of Formulae XXXIII, XXXIV and XXXV by methylation of the Compound of Formula II

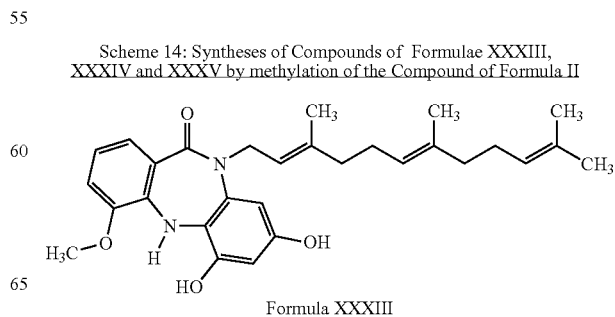

Formula XXXIII

-continued

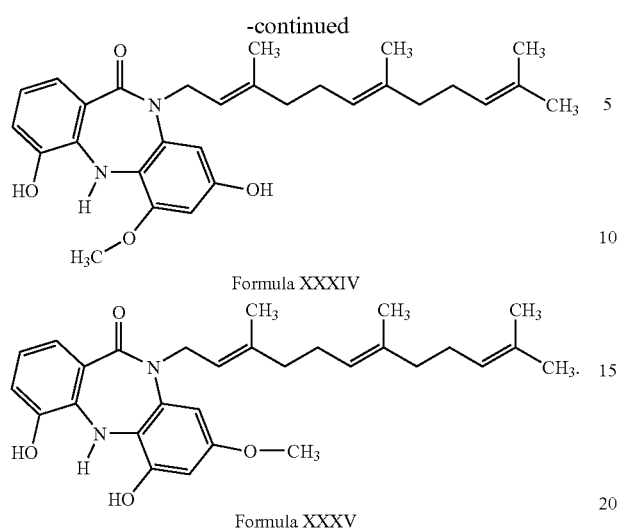

Formula XXXIV

Formula XXXV

A solution of the Compound of Formula XI (1 g) in tetrahydrofuran 50 (ml) is titrated with exactly one equivalent of sodium methoxide, allowed to stand for 30 minutes at room temperature and then treated with 1.2 equivalents of dimethylsulphate. Heat the mixture under reflux for one hour, cool to room temperature and pour into a mixture of toluene (200 ml) and water (200 ml). The layers are separated and the aqueous layer is extracted once more with an equal portion of toluene. The combined toluene layers are washed once with 1 N aqueous acetic acid and then concentrated to s crude product, which is predominantly a mixture of the Compounds of Formulae XXXIII, XXXIV and XXXV with some unchanged starting material and traces of over-methylated derivatives. The desired products may be separated and purified by HPLC or HSCC chromatography using the systems as described in Example 2 above, to obtain approximately 200 mg of each of the Compounds of Formulae XXXIII, XXXIV and XXXV.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

We claim:

1. A method of inhibiting the growth of a glioma cell, the method comprising contacting said glioma cell with a therapeutically effective amount of compound of formula II:

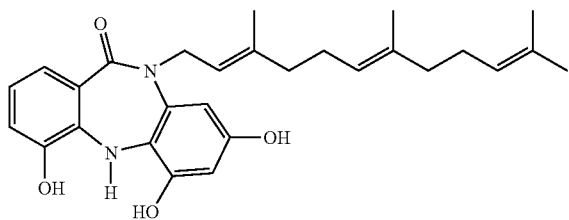

such that growth of said glioma cell is inhibited.

2. A method of inhibiting the growth of a glioma cell, the method comprising contacting said glioma cell with a therapeutically effective amount of a compound of formula I:

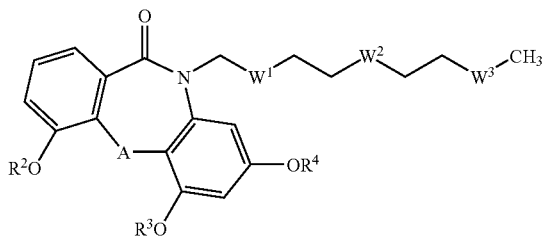

such that growth of said glioma cell is inhibited, wherein;

$W^1$, $W^2$ and $W^3$ is each independently selected from —CH=CH—;

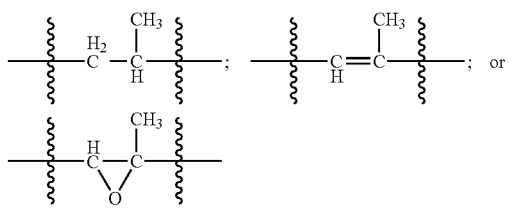

A is selected from —NH—, —NCH$_2$R$^1$, —NC(O)R$^1$;

R$^1$ is selected from C$_{1-6}$ alkyl, C$_{2-6}$ alkene, aryl or heteroaryl;

R$^2$, R$^3$, and R$^4$ is each independently selected from H, R$^5$, —C(O)R$^6$ R$^5$ is each independently selected from C$_{1-6}$ alkyl, C$_{2-7}$ alkalene, aryl or heteroaryl; and R$^6$ is each independently selected from H, C$_{1-6}$ alkyl, C$_{2-7}$ alkalene, aryl or heteroaryl.

3. The method of claim 2, wherein A of said compound is NH.

4. The method of claim 2, wherein A of said compound is —NCH$_2$R$^1$.

5. The method of claim 2, wherein A of said compound is —NC(O)R$^1$.

6. The method of claim 2, wherein R$^2$ of said compound is H.

7. The method of claim 2, wherein R$^3$ of said compound is H.

8. The method of claim 2, wherein R$^4$ of said compound is H.

9. The method of claim 2, wherein R$^2$, R$^3$ and R$^4$ of said compound are each H.

10. The method of claim 2, wherein R$^2$, R$^3$ and R$^4$ of said compound are each H, and W$^1$ is —CH=CH—.

11. The method of claim 2, wherein R$^2$, R$^3$ and R$^4$ of said compound are each H, and W$^2$ is —CH=CH—.

12. The method of claim 2, wherein R$^2$, R$^3$ and R$^4$ of said compound are each H, and W$^3$ is —CH=CH—.

13. The method of claim 2, wherein A of said compound is NH and R$^2$, R$^3$ and R$^4$ are each H.

14. The method of claim 2, wherein A of said compound is NH, and each of W$^1$, W$^2$, and W$^3$ is —CH=CH—.

15. A method of treating a glioma in a mammal, comprising the step of administering to said mammal a therapeutically effective amount of the compound of formula II:

such that said glioma is treated.

16. A method of treating a glioma in a mammal, comprising the step of administering a therapeutically effective amount of the compound of formula I to a mammal having a glioma:

such that said glioma is treated, wherein:

$W^1$, $W^2$ and $W^3$ is each independently selected from —CH=CH—

; or

A is selected from —NH—, —NCH$_2$R$^1$, —NC(O)R$^1$;

$R^1$ is selected from $C_{1-6}$ alkyl, $C_{2-6}$ alkene, aryl or heteroaryl;

$R^2$, $R^3$, and $R^4$ is each independently selected from H, $R^5$, —C(O)R$^6$ $R^5$ is each independently selected from $C_{1-6}$ alkyl, $C_{2-7}$ alkalene, aryl or heteroaryl; and $R^6$ is each independently selected from H, $C_{1-6}$ alkyl, $C_{2-7}$ alkalene, aryl or heteroaryl.

17. The method of claim 16, wherein A of said compound is NH.

18. The method of claim 16, wherein A of said compound is —NCH$_2$R$^1$.

19. The method of claim 16, wherein A of said compound is —NC(O)R$^1$.

20. The method of claim 16, wherein $R^2$ of said compound is H.

21. The method of claim 16, wherein $R^3$ of said compound is H.

22. The method of claim 16, wherein $R^4$ of said compound is H.

23. The method of claim 16, wherein $R^2$, $R^3$ and $R^4$ of said compound are each H.

24. The method of claim 16, wherein $R^2$, $R^3$ and $R^4$ of said compound are each H, and $W^1$ is —CH=CH—.

25. The method of claim 16, wherein $R^2$, $R^3$ and $R^4$ of said compound are each H, and $W^2$ is —CH=CH—.

26. The method of claim 16, wherein $R^2$, $R^3$ and $R^4$ of said compound are each H, and $W^3$ is —CH=CH—.

27. The method of claim 16, wherein A of said compound is NH and $R^2$, $R^3$ and $R^4$ are each H.

28. The method of claim 16, wherein A of said compound is NH, and each of $W^1$, $W^2$, and $W^3$ is —CH=CH—.

29. The method of claim 2, wherein said administering is oral.

30. The method of claim 2, wherein said administering is intravenous.

31. The method of claim 2, wherein said administering is intraperitoneal.

32. The method of claim 16, wherein said administering is oral.

33. The method of claim 16, wherein said administering is intravenous.

34. The method of claim 16, wherein said administering is intraperitoneal.

* * * * *